United States Patent [19]
Stern et al.

[11] Patent Number: 5,591,250
[45] Date of Patent: Jan. 7, 1997

[54] MATERIAL AND PROCESS FOR SEPARATING CARBON DIOXIDE FROM METHANE

[75] Inventors: S. Alexander Stern, Manlius, N.Y.; Hiroyoshi Kawakami, Hachioji, Japan; Ajay Y. Houde; Guangbin Zhou, both of Syracuse, N.Y.

[73] Assignee: Gas Research Institute, Chicago, Ill.

[21] Appl. No.: 368,995

[22] Filed: Jan. 5, 1995

Related U.S. Application Data

[63] Continuation-in-part of Ser. No. 104,345, Aug. 9, 1993, abandoned.

[51] Int. Cl.$^6$ .......................... B01D 53/22; B01D 71/64
[52] U.S. Cl. ....................................... 95/51; 96/14
[58] Field of Search ..................... 95/45, 51; 96/14

[56] References Cited

U.S. PATENT DOCUMENTS

| | | | |
|---|---|---|---|
| Re. 30,351 | 7/1980 | Hoehn et al. ................. | 55/16 |
| 3,816,303 | 6/1974 | Wrasidlo ................ | 210/500 X |
| 3,822,202 | 7/1974 | Hoehn ........................ | 210/23 |
| 4,113,628 | 9/1978 | Alegranti ................. | 210/500 |
| 4,378,324 | 3/1983 | Makino et al. ............ | 264/41 |
| 4,378,400 | 3/1983 | Makino et al. ............ | 428/220 |
| 4,690,873 | 9/1987 | Makino et al. ............ | 428/473.5 |
| 4,705,540 | 11/1987 | Hayes ...................... | 55/16 |
| 4,717,393 | 1/1988 | Hayes ...................... | 55/16 |
| 4,717,394 | 1/1988 | Hayes ...................... | 55/16 |
| 4,746,474 | 5/1988 | Kohn ........................ | 264/41 |
| 4,818,452 | 4/1989 | Kneifel et al. ............ | 264/41 |
| 4,838,900 | 6/1989 | Hayes ...................... | 55/16 |
| 4,929,405 | 5/1990 | Kohn ........................ | 264/41 |
| 4,931,182 | 6/1990 | Burgoyne et al. ........ | 210/500.39 |
| 4,952,220 | 8/1990 | Langsam et al. .......... | 210/500.39 X |
| 4,954,144 | 9/1990 | Burgoyne, Jr. et al. ... | 96/14 X |
| 4,978,430 | 12/1990 | Nakagawa ................. | 203/14 |
| 4,983,191 | 1/1991 | Ekiner et al. .............. | 96/14 |
| 4,988,371 | 1/1991 | Jeanes et al. .............. | 96/14 X |
| 5,039,417 | 8/1991 | Schucker .................. | 210/640 |
| 5,042,992 | 8/1991 | Blinka et al. .............. | 95/51 |
| 5,055,116 | 10/1991 | Kohn et al. ................ | 95/51 X |
| 5,067,970 | 11/1991 | Wang et al. ................ | 210/500.39 |
| 5,074,891 | 12/1991 | Kohn et al. ................ | 95/51 X |
| 5,076,816 | 12/1991 | Avrillon et al. ............ | 95/51 |
| 5,085,676 | 2/1992 | Ekiner et al. .............. | 210/500.39 X |
| 5,165,963 | 11/1992 | Matsumoto et al. ....... | 95/51 X |
| 5,178,650 | 1/1993 | Hayes ...................... | 95/51 X |
| 5,232,472 | 8/1993 | Simmons et al. .......... | 96/14 |
| 5,234,471 | 8/1993 | Weinberg .................. | 95/51 X |
| 5,248,319 | 9/1993 | Ekiner et al. .............. | 96/14 X |
| 5,266,100 | 11/1993 | Simmons ................... | 96/14 X |

OTHER PUBLICATIONS

Xuesong et al., "Gas Permeation Properties of Some Polypyrrolones", Journal of Membrane Science 88 (1994) 37–45.

*Primary Examiner*—Robert Spitzer
*Attorney, Agent, or Firm*—Harris Beach & Wilcox, LLP

[57] ABSTRACT

A process for separating a first gas from a second gas, having the steps of: (1) contacting one side of a semi-permeable gas separation membrane with a feed gas mixture containing at least the first gas and the second gas, wherein the membrane divides a separation chamber into a high-pressure side into which the feed gas mixture is fed and a low-pressure side; (2) maintaining a pressure differential across the membrane under conditions such that the first gas in the feed gas mixture selectively permeates through the membrane from the high-pressure side to the low-pressure side of the membrane; (3) removing from the low-pressure side of the membrane permeated gas mixture which is enriched in the first gas and depleted in the second gas; and (4) removing from the high-pressure side of the membrane a gas mixture which is enriched in the second gas and depleted in the first gas. The membrane used is made, at least in part, of a thin discriminating layer of polyimide having the repeating formula

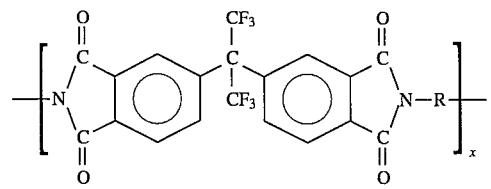

wherein R is:

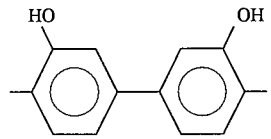

FORMULA 2

OR

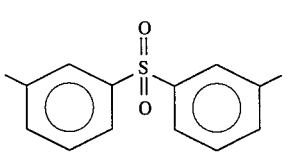

FORMULA 3

OR

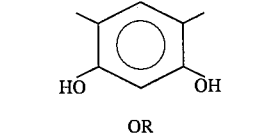

FORMULA 4

OR

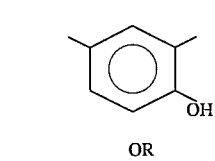

FORMULA 5

OR

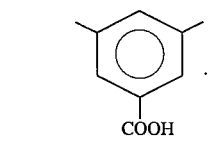

FORMULA 6

14 Claims, 1 Drawing Sheet

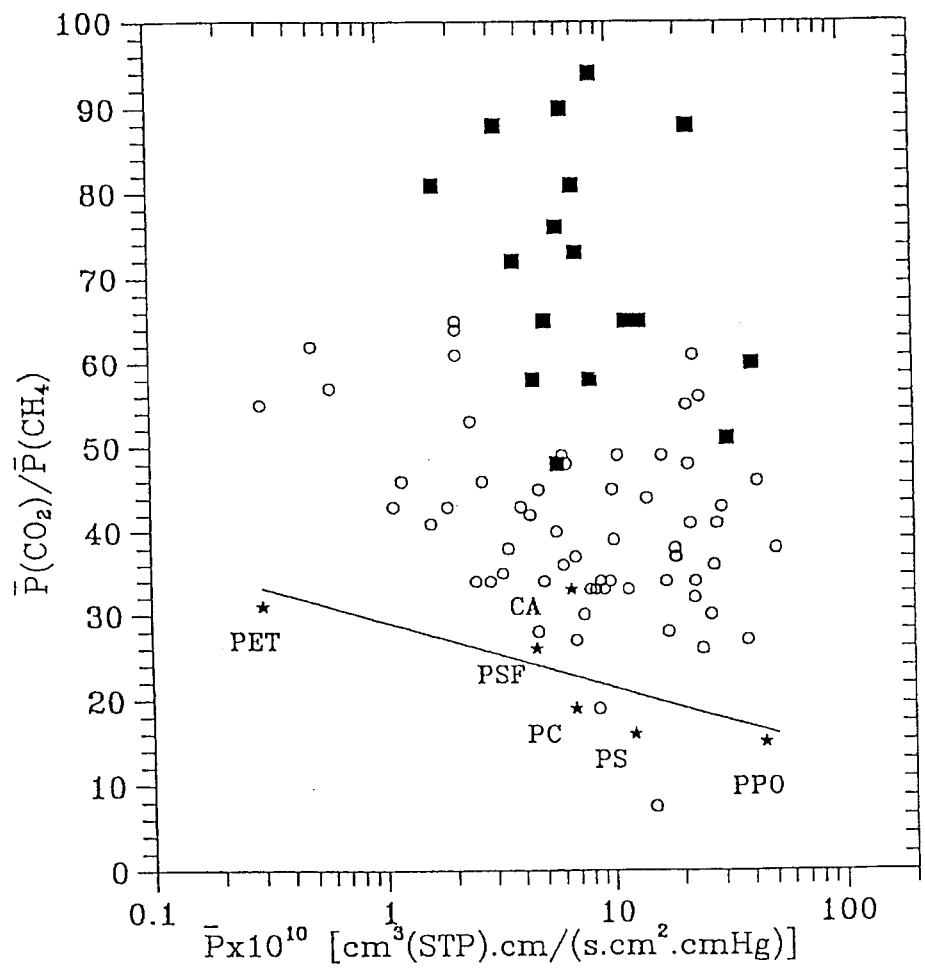
Figure 1: Relationship between $CO_2/CH_4$ selectivity and $CO_2$ permeability for various polymers at 95°F (35°C).
■: 6FDA-based polyimides developed at Syracuse University.
O: Polyimides reported in the literature.
★: Common polymers [PET = Poly(ethylene terephthalate); PSF = Polysulfone; CA = Cellulose Acetate; PC = Polycarbonate; PS = Polystyrene; PPO = Poly(phenylene oxide).]

5,591,250

MATERIAL AND PROCESS FOR SEPARATING CARBON DIOXIDE FROM METHANE

This application is a continuation-in-part of U.S. application Ser. No. 08/104,345 filed on Aug. 9, 1993 now abandoned.

BACKGROUND OF THE INVENTION

This invention relates to an improved material and process for separating carbon dioxide from methane. More particularly this invention relates to new polyimide polymers and the process for using both new and known polyimide polymers for separation of carbon dioxide from methane.

SUMMARY OF THE INVENTION

The use of membrane separation processes is a well-established technology. The process essentially involves contacting one side of a semi-permeable gas separation membrane with a feed gas mixture containing at least the gas whose enrichment is desired, along with one or more other gases. The membrane divides a separation chamber into a high-pressure side into which the feed gas mixture is fed and a low-pressure side. A pressure differential is maintained across the membrane under conditions such that at least one but less than all the gases in the feed gas mixture selectively permeates through the membrane from the high-pressure side to the low-pressure side of the membrane. Then the gas mixture which is relatively enriched in a first group of gases (i.e. one or more gases) and depleted in a second, different, group of gases (i.e. one or more different gases) is removed from the low-pressure side of the membrane, while a gas mixture which is enriched in the second group of gases and depleted in the first group of gases is removed from the high-pressure side of the membrane.

In the past three decades there have been numerous advances in the use of membranes for the separation of gases. This has become a commercially viable technique; well over a hundred membrane separation installations operate in the U.S. and abroad.

Of particular commercial importance is the removal of carbon dioxide from natural gas, leaving the desirable methane in higher concentration. This process, if performed effectively, can upgrade low quality natural gas to high grade natural gas. The standard membrane used for such separation, when the gases of interest are $CO_2$ and $CH_4$ is cellulose acetate. It is against cellulose acetate that the commercial viability of any other membrane must be judged.

The effectiveness of a separation process is judged by a number of factors. One is the throughput in terms of volume of gas processed per unit time. Another is the efficiency in terms of the constitution of the final product as compared to the constitution of the product initially fed into the system.

Membranes act to separate gases by virtue of gas permeation. Permeation describes the overall mass transport of "penetrant gas" across the membrane where the penetrant gas is introduced at a higher pressure than the pressure on the opposite side of the membrane. The gas mixture being separated is known as the feed, that which passes through the membrane is the permeate, and that which does not pass through the membrane is the retentate. In the separation process, the membrane being used exhibits a higher selectivity for one component, say A than the other, say B. A permeates faster than B, hence relative to the feed, the permeate is enriched in A and the retentate is enriched in B.

The extent of separation achievable depends upon the following factors: feed composition, the nature of the membrane, the pressures $P_h$ and $P_l$, which are the pressures on the feed side and permeate side of the membranes, respectively, temperature, stage cut (the fraction of the feed permeating through the membrane) and the flow pattern of the high and low pressure streams in the permeator. Methods of controlling temperature and pressure are well known in the art as are various techniques to enhance the extent of separation as, for example, using asymmetric membranes, recycling permeators, continuous membrane columns and multimembrane permeators.

The gas permeability of a polymer membrane toward a gas A is characterized by a mean "permeability coefficient", $\bar{P}(A)$, which is a function of the nature of the gas and the polymer membrane, the temperature, and, in the most general case, the gas pressures maintained on each side of the membrane. Where a gas A is a component of a mixture, rather than being pure, $\bar{P}(A)$ may also be dependent upon the composition of the mixture. Permeability coefficients are commonly expressed in units of $cm^3(STp) \cdot cm/(s \cdot cm^2 \cdot cmHg)$. The selectivity of a polymer membrane toward a gas A relative to another gas B is generally expressed by an "ideal separation factor", $a^*(A/B)$, which is defined by the relation:

$$a^*(A/B) = \bar{P}(A)/\bar{P}(B)$$

where the permeability coefficients $P(A)$ and $P(B)$ for gases A and B, respectively, are measured under comparable conditions. $a^*(A/B)$ is dimensionless.

The focus of the instant invention is on the development and use of a membrane which exhibits a high degree of selectivity for carbon dioxide as compared with methane. In particular polyimides have been developed and tested that exhibit a selectivity toward carbon dioxide relative to methane, as well as a relatively high permeability of carbon dioxide, and thus are effective for use in permeation.

The prior art discloses a number of polymers, including polyimide polymers which have been used to separate carbon dioxide from methane, along with a number of polyimides which were examined but for which no data was obtained with respect to their exhibiting a higher selectivity toward carbon dioxide with respect to methane.

Thus, for example U.S. Pat. No. Re. 30,351 to Hoehn et al. discloses the structure of 6FDA-2,4-DABAc but does not teach or suggest its use to separate $CO_2$ from $CH_4$.

An article in the literature, namely T. M. Moy and J. E. McGrath, *J. Polym. Sci., Polym. Chem. Ed.*, 32, 1903 (1994) discloses the structure of 6FDA-2,4-DARsol but does not teach or suggest its use to separate $CO_2$ from $CH_4$.

U.S. Pat. No. 4,705,540 to Hayes describes certain substituted aromatic polyimide gas separation membranes used in gas separation membranes.

U.S. Pat. No. 4,978,430 to Nakagawa et al. describes an aromatic polyimide gas separation membrane used for separation of water vapor from organic compound vapor.

U.S. Pat. No. 4,690,873 to Makino et al. discloses an aromatic imide polymer used to separate carbon dioxide from one of a number of other gases, of which one is methane.

U.S. Pat. No. 4,717,393 to Hayes shows cross-linked polyimide gas separation membranes, exhibiting very high permeation to gases.

U.S. Pat. No. 4,983,191 to Ekiner et al. discloses a method of production of aromatic polyimide membranes. They were not tested for $CO_2/CH_4$ selectivity.

U.S. Pat. No. 5,085,676 to Ekiner et al. concerns a process for preparing multicomponent gas separation membranes.

U.S. Pat. No. 5,067,970 to Wang et al. discloses a number of asymmetric polyimide membranes based on a fully imidized 5(6)-amino-1-(4'-aminophenyl)-1,3-trimethylindane polymer.

U.S. Pat. No. 4,952,220 to Langsam et al. discusses polyimide membranes, with surface modifiable units used for $O_2/N_2$ separation.

Polyimide gas separation membranes and their preparation are also shown in U.S. Pat. No. 4,838,900 to Hayes, U.S. Pat. No. 4,378,400 to Makino et al., U.S. Pat. No. 4,931,182 to Burgoyne, Jr. et al., U.S. Pat. No. 4,378,324 to Makino et al., U.S. Pat. No. 4,746,474 to Kohn, U.S. Pat. No. 3,816,303 to Wrasidlo, U.S. Pat. No. 3,822,202 to Hoehn, U.S. Pat. No. 4,133,628 to Alegranti, U.S. Pat. No. 4,929,405 to Kohn, U.S. Pat. No. Re. 30,351 to Hoehn et al., and U.S. Pat. No. 4,717,394 to Hayes. These patents are incorporated by reference as to their disclosure of a general methodology for separating gases using membranes.

The majority of the polyimides of the instant invention were not disclosed in any of the above references. The two that were disclosed, namely 6FDA-2,4-DARsol and 6FDA-2,4-DABC have not been tested with respect to separation of $CO_2$ from $CH_4$.

It is well known in the field that the selectivity of a given polymer membrane for a given gas relative to another gas depends in the most general case on the structure of the polymer, the morphology of the membrane, the temperature, the gas composition, and the gas pressures maintained on opposite membrane surfaces. The gas selectivity must be determined experimentally for each condition and cannot be predicted at present from knowledge of any or all of the above factors alone. Moreover, it is not possible to predict the gas selectivity of a polymer (or of a polymer membrane) for a given pair of gases under a given set of conditions from a knowledge of the selectivity of another pair of gases, even under the same conditions (e.g. temperature, pressure). For example the $O_2/N_2$ selectivity of a given polymer (i.e. the selectivity for $O_2$ relative to $N_2$) cannot be predicted from the $O_2/CO_2$, $CO_2/N_2$, $CO_2/CH_4$, $H_2/CH_4$, etc., selectivity or from any other selectivity, and vice versa, even under the same conditions. Nor is it possible to predict the selectivity of a polymer to a given gas pair from that of another polymer having a different chemical structure to the same or to a different gas pair, even under the same conditions. It is similarly not possible to predict the intrinsic permeability of a polymer (or polymer membrane) to a given gas or gas mixture under any condition (the intrinsic permeability of a polymer to a given gas is characterized by a permeability coefficient). Similarly, the gas permeability of polymers (or polymer membranes) can be determined at present only experimentally.

This inherent unpredictability of membrane selectivity and permeability applies to members of a family of polyimide membranes. In the case where members of a given class of compounds tend to show favorable selectivity and permeability characteristics regarding a given gas mixture, it is nevertheless not possible without experimentation to predict that another member of the class would have superior characteristics.

The instant invention relates to a group of polyimides which exhibit both a high permeability toward $CO_2$ and a high degree of selectivity of $CO_2$ relative to —$CH_4$.

It is therefore a primary object of the present invention to provide a gas separating material exhibiting a high degree of selectivity of $CO_2$ relative to $CH_4$.

It is another object of the present invention to provide a gas separating material exhibiting both a high permeability toward $CO_2$ and a high degree of selectivity of $CO_2$ relative to $CH_4$.

It is yet another object of this invention to provide a gas separating material exhibiting both a high permeability toward $CO_2$ and a high degree of selectivity of $CO_2$ relative to $CH_4$ where the polymers forming the gas separating material are soluble in common organic solvents and can readily be cast in the form of thin membranes (films).

These and other objects of the present invention are attained by a process for separating a first gas from a second gas, having the steps of: (1) contacting one side of a semi-permeable gas separation membrane with a feed gas mixture containing at least the first gas and the second gas, wherein the membrane divides a separation chamber into a high-pressure side into which the feed gas mixture is fed and a low-pressure side; (2) maintaining a pressure differential across the membrane under conditions such that the first gas in the feed gas mixture selectively permeates through the membrane from the high-pressure side to the low-pressure side of the membrane; (3) removing from the low-pressure side of the membrane permeated gas mixture which is enriched in the first gas and depleted in the second gas; and (4) removing from the high-pressure side of the membrane a gas mixture which is enriched in the second gas and depleted in the first gas. The membrane used is made, at least in part, of a thin discriminating layer of polyimide having the repeating formula:

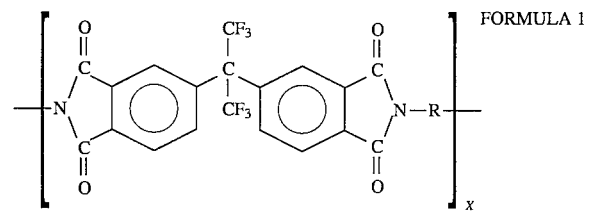

FORMULA 1 wherein R is:

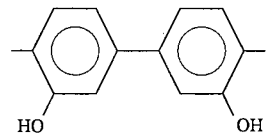

FORMULA 2

OR

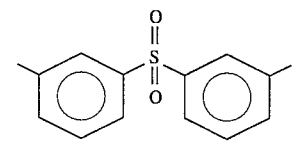

FORMULA 3

OR

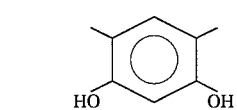

FORMULA 4

OR

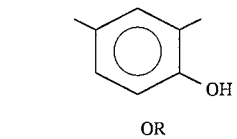

FORMULA 5

OR

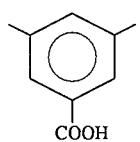

FORMULA 6 and x is an interger.

BRIEF DESCRIPTION OF THE DRAWINGS

The above-mentioned and other features and objects of this invention, and the manner of obtaining them, will be more apparent and the invention itself will be better understood by reference to the following description of the invention, taken in conjunction with the accompanying Drawing, wherein:

FIG. 1 is a graph showing the relationship between $CO_2/CH_4$ selectivity and $CO_2$ permeability for various polymers at 95° F. (35° C.).

DETAILED DESCRIPTION OF THE PREFERRED EMBODIMENTS

The present invention was motivated by the desire to create membranes that function in the removal of undesirable compounds, specifically $CO_2$ from natural gas. Polyimide polymers were chosen as the focus of the research because of their high gas selectivity, good mechanical properties and versatile chemistry.

This invention provides a group of polyimide polymers which exhibit both a high selectivity toward $CO_2$ relative to $CH_4$ as well as a high permeability to $CO_2$. The selectivity toward $CO_2$ relative to $CH_4$ of these polyimide polymers is much higher than that of commercially available polymers having similar permeability to $CO_2$.

Polyimides are made from two monomers: a dianhydride and a diamine. The preferred polyimide polymers for the gas separating membrane all have the same fluorine-containing dianhydride, 6FDA:

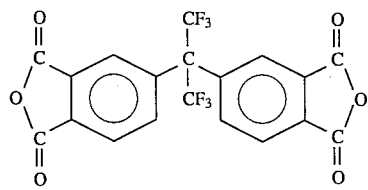

FORMULA 7 and different diamines.

Polyimides 1–6 are homopolymers, 7–11 copolymers, and 12–13 are blends. The chemical designations of the homopolymers and the polyimides used for the preparation of the blends, all of which have been prepared and tested in our laboratory, are listed in Tables I, II and II. In all formulas shown herein x and y are integers.

TABLE I

Chemical Designation of Homopolymer Polyimides

| | |
|---|---|
| 6FDA-HAB | Poly[2,2-bis(3,4-dicarboxyphenyl) hexafluoropropane diimino hydroxy benzidine] |
| 6FDA-3,3'-DABz | Poly[2,2-bis(3-carboxyphenyl) hexafluoropropane imidiazo 3,3'-benzidine] |
| 6FDA-3,3'-DDS | Poly[2,2'-bis(3,4-dicarboxyphenyl) hexa- |

TABLE I-continued

Chemical Designation of Homopolymer Polyimides

| | |
|---|---|
| | fluoropropane diimino 4,4'-diphenysulfone] |
| 6FDA-2,4-DAPhol | Poly[2,2-bis(3,4-dicarboxyphenyl) hexafluoropropane 2,4-diaminophenol] |
| 6FDA-3,5-DABAc | Poly[2,2-bis(3,4-dicarboxyphenyl) hexafluoropropane 3,5-diaminobenzoic acid] |
| 6FDA-2,4-DARsol | Poly [(1,3-dihydro-1,3-dioxo-2H-isoindole-2,5-diyl)-2,2,2-trifluoro-1-(trifluoromethyl)-ethylidene-(1,3-dihydro-1,3-dioxo-2H-isoindole-2,5-diyl)-2,4-dihydroxyphenylene] |

TABLE II

Chemical Designation of Copolymer Polyimides

| | |
|---|---|
| 6FDA-4,4'-ODA/DABA(1:1) | Poly[2,2'-bis(3,4-dicarboxyphenyl) hexafluoropropane diimino 4,4'-oxydiamine co 2,2-bis(3,4-dicarboxyphenyl) hexafluoropropane diimino 3,5-benzoic acid(1:1)] |
| 6FDA-4,4'-ODA/DABS(1:1) | Poly[2,2'-bis(3,4-dicarboxyphenyl) hexafluoropropane diimino 4,4'-oxydiamine co 2,2-bis(3,4-dicarboxyphenyl) hexafluoropropane diimino 2,5-benzenesulfonic acid(1:1)] |
| 6FDA-1,3-PDA/3,3'-DDS (1:1) | Poly[(1,3-dihydro-1,3-dioxo-2H-isoindole-2,5-diyl)-2,2,2-trifluoro-1-(trifluoromethyl)ethylidene-(1,3-dihydro-1,3-dioxo-2H-isoindole-2,5-diyl)-1,3-phenylene-co-3,3'-phenylenesulfone] |
| 6FDA-BisAPAF/HAB (1:1) | Poly[(1,3-dihydro-1,3-dioxo-2H-isoindole-2,5-diyl)-2,2,2-trifluoro-1-(trifluoromethyl)ethylidene-(1,3-dihydro-1,3-dioxo-2H-isoindole-2,5-diyl)-2,2'-bis(4-hydroxyphenyl)-2,2,2-trifluoro-1-(trifluoromethyl)ethylidene-co-3,3'-dihydroxy benzidine] |
| 6FDA-2,4-DAPhol/1,3-PDA (3:1) | Poly[(1,3-dihydro-1,3-dioxo-2H-isoindole-2,5-diyl)-2,2,2-trifluoro-1-(trifluoromethyl) ethylidene-(1,3-dihydro-1,3-dioxo-2H-isoindole-2,5-diyl)-2,4-phenol-co-1,3-phenylene] |

TABLE III

Chemical Designation of Polyimides used for the Preparation of Blends

| | |
|---|---|
| 6FDA-3,3'-DDS | Poly[2,2-bis(3,4-dicarboxyphenyl) hexafluoropropane 3,3'-diaminodiphenlysulfone] |
| 6FDA-1,3-PDA | Poly[2,2-bis(3,4-dicarboxyphenyl) hexafluoropropane 1,3-diaminophenylene] |
| 6FDA-1,3,5-TrMPDA | Poly[2,2-bis(3,4-dicarboxyphenyl) hexafluoropropane 3,4-diamino-1,3,5-trimethylphenylene] |

Synthesis of Polyimide Homopolymers—First Group

The first group consisted of the first three homopolymers listed and the first two copolymers listed. The method involves thermal imidization which results in polyimides that are insoluble in most organic solvents and are not readily cast in the form of membranes (films).

A. Monomers and Solvents

In synthesizing the first five polymers and the first two copolymers, the monomers used, namely, 6FDA [2,2-bis(-3,4-decarboxyphenyl) hexafluoropropane dianhydride]; HAB [3,3'-hydroxy diaminobenzidine (3.3'-DABz) (3,3'-diaminobenzedene); 1,4,-PDA(para-phenylene diamine]; and 1,3-PDA (meta-phenylene diamine) were obtained in sufficiently pure form so as not to require further purification. The monomer m-DDS(3,3'-diamino-diphenylsulfone) was purified by recrystallization from a solution in ethanol.

DMAc(N,N'-dimethylacetamide) was used as solvent without further purification and was stored in the dark. Pyridine was used as a solvent without further purification.

B. Experimental Technique

All syntheses were performed in a reaction vessel—an apparatus which consisted of a 4-neck round-bottomed flask provided with a stirrer, a thermometer, an adapter covered with heating tape connecting the flask to a Liebig condenser, and a connection to allow continuous purging of the contents with dry nitrogen gas.

(1) Synthesis of 6FDA-HAB by the first method.

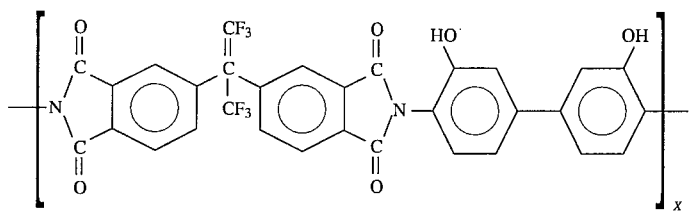

FORMULA 8

6FDA-HAB was prepared by polycondensation followed by thermal imidization. A solution of 0.020 moles (4.325g) of HAB in 50 ml DMAc was poured into the reaction vessel. A solution containing 0.020 moles (8.883g) of 6FDA in 50 ml DMAc was then slowly added (1–2 drops/sec) through a separatory funnel to the HAB solution with constant stirring at room temperature. The resulting mixture was stirred for 7 hours at room temperature, while the reaction vessel was continuously purged with nitrogen, until polymerization was completed. This reaction produced a solution of 6FDA-HAB polyamic acid.

Membranes were prepared from a 10% solution of 6FDA-HAB polyamic acid in DMAc. This solution was cast onto a Teflon plate and the solvent was allowed to evaporate in a vacuum oven at about 80° C. The membranes formed after the solvent evaporated were allowed to cool to room temperature and were removed from the Teflon plate. The membranes were then cured (imidized) by heating in the vacuum oven, first at 200° C. for 4 hours, next at 250° C. for about 1 hour, and finally at 300° C. for 2 hours.

(2) Synthesis of 6FDA-3,3'-DABz by the first method:

Membranes were prepared from 6FDA-3,3'-DABz by the same method as described above for the preparation of 6FDA-HAB membranes. However, four curing conditions were investigated because different curing conditions were found to yield different polymer structures with different gas permeabilities and selectivities. The best curing procedure of those examined was to heat the 6FDA-3,3'-DABz membranes in a vacuum oven at 300° C. for at least 24 hours.

(3) Synthesis of 6FDA-3,3'-DDS (or 6FDA-m-DDS) by the first method:

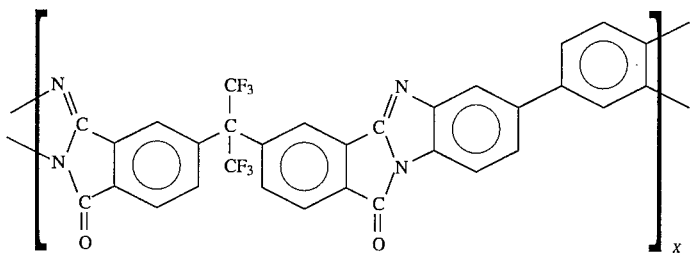

FORMULA 9

6FDA-3,3'-DABz was synthesized by the method described above for 6FDA-HAB. A solution of 0.020 moles (4.284 g) of 3,3'-DABz in 60 ml DMAc and a solution of 0.020 moles (8.883 g) of 6FDA in 50 ml DMAc were used for this purpose.

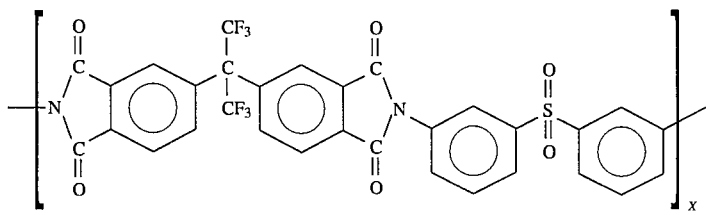

FORMULA 10

6FDA-3,3'-DDS was prepared by polycondensation followed by chemical imidization. A solution of 0.020 moles (4.325 g) of 3,3'-DDS in 65 ml DMAc was poured into the reaction vessel. A solution containing 0.020 moles (9.8983g) of 6FDA in 65 ml DMAc was then slowly added, through a separatory funnel, to the 3,3'-DDS solution under constant stirring at 60° C. The resulting mixture was stirred for 3 hours at 60° C., while the reaction vessel was continuously purged with nitrogen, at which time polymerization was completed. A quantity of 0.10 moles (9.41 ml) acetic anhydride and 0.10 moles (13.4 ml) triethylamine was then added to the polyamic acid solution formed by the above polymerization reaction. Stirring was continued for 16 hours at 60° C. until the polyamic acid was converted to 6FDA-3,3'-DDS polyimide. The polyimide solution was then slowly poured into a vessel containing 2000–3000 ml methanol. The polyimide 6FDA-m-DDS thus precipitated was then filtered from the solution, dried, redissolved in DMAc, and precipitated again with methanol. Finally, the polyimide was filtered from solution and dried in a vacuum oven at 80° C. for 2 days.

Membranes were prepared from a 10% solution of 6FDA-3,3'-DDS polyimide in DMAc. This solution was cast onto glass plates and the solvent was allowed to evaporate in a vacuum oven at 80° C. for 16 hours. The membranes were allowed to cool to room temperature and were then removed from the glass plates. The membranes were finally heated in a vacuum oven at 150° C. for 48 hours to remove all residual solvent.

II. Synthesis of Polyimide Copolymers

A. Monomers and Solvents

The monomers and solvent required for the synthesis of the copolymers were purified prior to use as follows:

6FDA [2,2-bis(3,4-dicarboxyphenyl)hexafluoropropane dianhydride] was sublimated twice at 200°–210° C. at a pressure of less than 1 Torr.

4,4'-ODA(4,4'-oxydiamine), or p-ODA, was sublimated twice at 180° C. at a pressure of less than 1 Torr.

DABAc (3,5-diaminobenzoic acid) and DABS (2,5-diaminobenzenesulfonic acid) were each recrystallized twice from water.

Acetic anhydride was used as an imidization agent without further purification.

NMP(N-methyl pyrrolidinone), used as solvent without further purification, was stored under dry nitrogen. Toluene and methanol were also used as solvents without further purification.

(1) Synthesis of 6FDA-4,4'-ODA-DABAc (1:1)

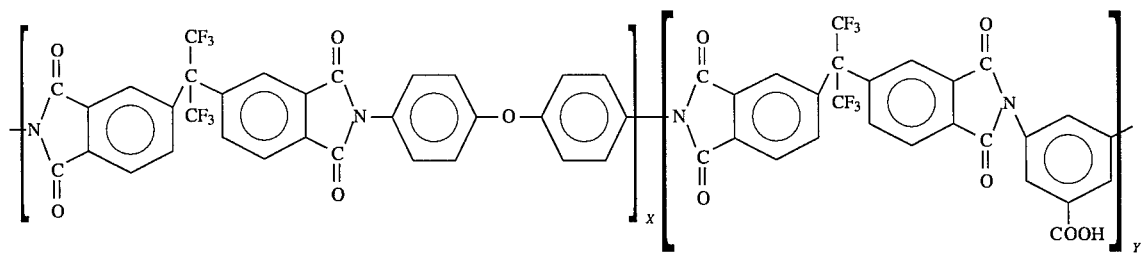

FORMULA 11 and 6FDA-4,4'-ODA/DABS (1:1)

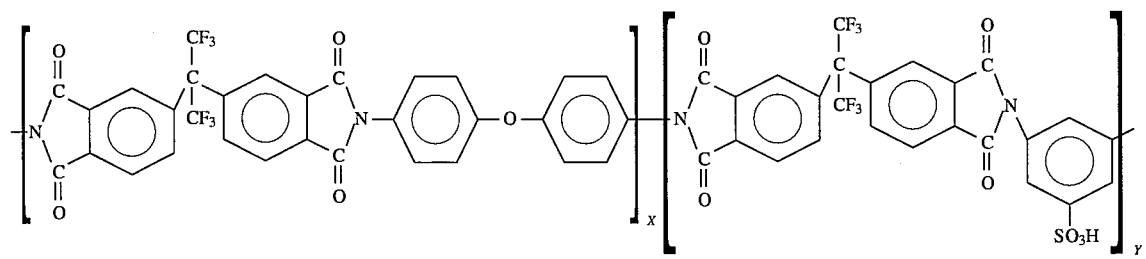

FORMULA 12

(Note: the general formulas x and y are given. In the synthesized copolymers, x and y are both 1.) Polyimide copolymers were prepared by polycondensation followed by thermal imidization. The reaction vessel—an apparatus which consisted of a 4-neck round-bottomed flask which was fitted with a stirrer, a thermometer, an adapter covered with heating tape connecting the flask with a Liebig condenser, and a connection for providing a continuous nitrogen purge. A solution containing 0.005 moles (1.001g) of p-ODA and 0.005 moles of DABAc (0.761 g) or DABS (0.941 g) in 30 ml of NMP was poured into the reaction vessel. A solution of 0.01 moles (4.443 g) of 6FDA in 20 ml NMP was then added slowly at room temperature. After stirring continuously for one day at room temperature, 60 ml toluene was added to the reaction vessel and the resulting solution was stirred at 180° C. for 4 hrs.

To form membranes, the solution resulting from the above operations was poured into a Petri dish and dried in an oven at 80° C. The membranes thus obtained were removed from the Petri dish and further dried in a vacuum oven at 250° C. for one day.

corresponding polyimide; these were stored on potassium hydroxide pellets. Acetone, dichloromethane, chloroform, methylethylketone (MEK), and methylenechloride, all used as solvents for the preparation of the membranes (films), were used without further purification. All the solvents mentioned above had a minimum purity of 99%.

B. Experimental Techniques

All syntheses were performed in a reaction vessel—an apparatus which consisted of a 4-neck round-bottomed flask equipped with a mechanical stirrer, thermometer, nitrogen inlet and a Liebig condenser. An oil bath was used to maintain the reaction temperature.

(1) Synthesis of Polyimide Homopolymers and Membrane Preparation 6FDA-HAB

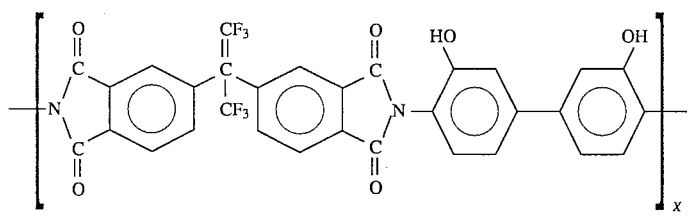

FORMULA 8

III Synthesis of Polyimide Homopolymers and Membrane Preparation—Second Group:

The second group consisted of the fourth, fifth and sixth polyimide homopolymers, the third through fifth copolymers and the polyimides for the blend. In addition the first polyimide, namely 6FDA-HAB, was synthesized by alternate means, namely chemical imidization, which yields polymers that are soluble in common organic solvents and can readily be cast in the form of membranes.

A. Monomers and Solvents

The fluorine-containing dianhydride 6FDA (99.5%) [2,2-bis-(3,4-dicarboxyphenyl) hexafluoropropane dianhydride] used in the polyimide syntheses was purified by vacuum sublimation before use. The diamines, namely, HAB [3,3'-dihydroxy-4,4'-diamino benzidine]; 2,4-DAPhol [2,4-diaminophenol]; 3,5-DABAc [3,5-diamino benzoic acid]; 1,3,5-TrMPDA [1,3,5-trimethyl phenylene diamine]; 1,3-PDA [meta-phenylene diamine]; 2,4-DARsol [2,4-diaminoresorsinol]; 1,3-PDA [metaphenylenediamine]; BisAPAF [2,2'-bis(3-amino-4 hydroxyphenyl) hexafluoro propane]; and 2,4-DAPhol.2HCI [2,4-diaminophenol (salt)] were obtained at sufficient purity not to require further purification. The monomer 3,3'-DDS [meta-diamino-diphenylsulfone] was purified twice by recrystallization from ethanol solution.

DMAc (N,N'-dimethylacetamide ), NMP (1-methyl-2-pyrrolidone ), toluene, TEA (triethylamine), and acetic anhydride were used as solvents without further purification. DMAc, NMP, and toluene were graded as anhydrous reagents and stored in the dark on molecular sieves. The solvents acetic anhydride and triethylamine acted as a dehydrating agent and catalyst, respectively, during the intramolecular cyclodehydration of the polyamic acid to yield the This polyimide was prepared by a polycondensation followed by high-temperature solution imidization. In a reaction vessel, 0.02 moles (4.325 g) of HAB were dissolved over a thirty minute period in 40 ml NMP at room temperature under constant purge of dry nitrogen. A quantity of 0.02 moles (8.885 g) of 6FDA was added at once to the diamine solution with vigorous stirring. The flask was rinsed with an additional 30 ml NMP. The resulting mixture was stirred for 4 hours at room temperature, with the reaction mixture vessel being continuously purged with dry nitrogen. This reaction produced a solution of 6FDA-HAB polyamic acid.

The 6FDA-HAB polyamic acid was diluted with 50 ml NMP and stirred for 30 minutes. A quantity of 0.10 moles (10.8 ml) toluene (as a low boiling azeotropic agent) was added to the resulting mixture, and azeotropic distillation was performed at 130°–140° C. Stirring was continued at 150° C. for 4 hours. The solution was gradually cooled to room temperature. The resulting polyimide solution was then slowly poured into a vessel containing 1500 ml methanol. The polyimide 6FDA-HAB thus precipitated, was then filtered from the solution, dried, redissolved in NMP, and precipitated, again using methanol. Finally, the polyimide was filtered from solution and dried at 150° C. in an air oven for 24 hours and then in a vacuum oven for 48 hours.

Membranes were prepared from a 5–7 wt-% solution of 6FDA-HAB polyimide in acetone. This solution was cast on a Petri dish and the solvent was allowed to evaporate at room temperature for 24 hours. The membranes were removed by immersing the Petri dish in hot water, and then dried in a vacuum oven at 100° C., 150° C., 200° C., and 250° C. for 6 hours at each temperature, with a final drying, before use, at 300° C. for 24 hours.

(2) 6FDA-2,4-DAPhol

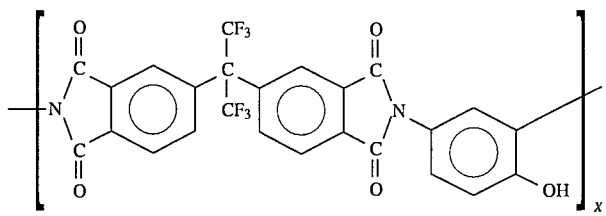

FORMULA 13

This polyimide was synthesized by polycondensation followed by high-temperature solution imidization. In a reaction vessel, 0.02 moles (2.949 g) of 2,4-DAPhol.2HCl salt was dissolved in 30 ml NMP at room temperature under constant purge of dry nitrogen. To this solution an equimolar amount of $Li_2CO_3$ (1.478 g) in 10 ml NMP was added to neutralize the salt solution, and the resultant solution was stirred for 30 minutes. A quantity of 0.020 moles (8.885 g) of 6FDA was added in two batches to the diamine solution while stirring vigorously. The flask was rinsed with an additional 40 ml NMP. The resulting mixture was stirred for 12 hours at room temperature, with the reaction mixture vessel being continuously purged with dry nitrogen. This reaction produced a solution of 6FDA-2,4-DAPhol polyamic acid.

A quantity of 0.28 moles (30 ml) toluene (as a low boiling azeotropic agent) was added to the polyamic acid solution, and azeotropic distillation was performed at 150°–160° C. Stirring was continued at 150° C. for 12 hours. The solution was gradually cooled to room temperature. The resulting polyimide solution was then added dropwise into a vessel containing 1200 ml methanol. The polyimide 6FDA-2,4-DAPhol thus precipitated, was then filtered from the solution, washed with methanol several times, and dried at room temperature in an air oven for 24 hours and then at 170° C. in a vacuum oven for 48 hours.

Membranes were prepared from a 6 wt-% solution of 6FDA-2,4-DAPhol polyimide in acetone. This solution was cast on a Petri dish and the solvent was allowed to evaporate at room temperature for 24 hours. The membranes obtained were dried in a vacuum oven first at 100° C. and then at 150° C. for 12 hours each, with a final drying before use at 200° C. for 48 hours.

(3) 6FDA-3,5-DABc

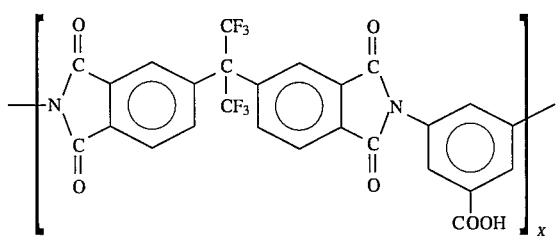

FORMULA 14

This polyimide was prepared by polycondensation followed by high-temperature solution imidization. In a reaction vessel, 0.02 moles (3.043 g) of 3,5-DABAc was dissolved in 30 ml NMP at room temperature under constant purge of dry nitrogen. A quantity of 0.020 moles (8.883 g) of 6FDA was added at once to the diamine solution while stirring vigorously. An additional 30 ml of NMP was added to the viscous reaction mixture. The resulting mixture was stirred for 8 hours at room temperature, with the reaction vessel being continuously purged with dry nitrogen. A solution of 6FDA-3,5-DABAc polyamic acid was thus produced.

A quantity of 0.28 moles (30 ml) toluene (as a low boiling azeotropic agent) was added to the 6FDA-3,5-DABAc polyamic acid and azeotropic distillation was performed at 150°–160° C. Stirring was continued at 150° C. for 6 hours. The solution was gradually cooled to room temperature. The resulting polyimide solution was then added dropwise to a vessel containing 1200 ml methanol. The polyimide 6FDA-3,5-DABAc thus precipitated was then filtered from the solution, and dried first at room temperature in an air oven for 24 hours and then in a vacuum oven at 150° C. for 48 hours.

Membranes were prepared from a 6 wt-% solution of 6FDA-3,5-DABAc polyimide in acetone. This solution was cast on a Petri dish and the solvent was allowed to evaporate at room temperature for 24 hours. The membranes obtained were dried in a vacuum oven first at 100° C. and then at 150° C. for 12 hours each, with a final drying before use at 200° C. for 24 hours.

(4) 6FDA-2,4-DARsol

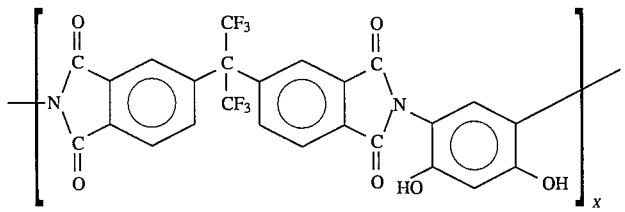

FORMULA 15

This polyimide was synthesized by polycondensation followed by high-temperature solution imidization. In a reaction vessel, 0.02 moles (4.261 g) of 2,4-DARsol.2HCl salt was dissolved in 30 ml NMP at room temperature under constant purge using dry nitrogen. To this solution an equimolar amount of Li$_2$CO$_3$ (1.478 g) in 10 ml NMP was added to neutralize the salt solution. The resulting solution was stirred for 30 minutes. A quantity of 0.02 moles (8.885 g) of 6FDA was added at once to the diamine solution while stirring vigorously. An additional 20 ml of NMP was added to the reaction mixture. The resulting mixture was stirred for 12 hours at room temperature while the reaction vessel was continuously purged with dry nitrogen. This reaction produced a solution of 6FDA-2,4-DARsol polyamic acid.

A quantity of 0.28 moles (30 ml) toluene, as a low boiling azeotropic agent, was added to the polyamic acid solution and azeotropic distillation was then performed at 150°–160° C. Stirring was continued at 170° C. for 4 hours. The solution was gradually cooled to room temperature. The resulting polyimide solution was then added dropwise to a vessel containing 1200 ml methanol. The polyimide 6FDA-2,4-DARsol thus precipitated was filtered from the solution, washed with methanol several times, and dried first at room temperature for 24 hours and then at 130° C. in a vacuum oven for 12 hours.

Membranes were prepared from a 6 wt-% solution of 6FDA-2,4-DARsol polyimide in methylethylketone. This solution was cast on a Petri-dish and the solvent was allowed to evaporate at room temperature for 24 hours. The membranes obtained were dried in a vacuum oven at 100° C. and 150° C. for 12 hours each, and finally at 200° C. for 48 hours before use.

C: Synthesis of Polyimide Copolymers and Membrane Preparation (1) 6FDA-1,3-PDA/3,3'-DDS (1:1)

0.10 moles (13.4 ml) triethylamine were then added to the polyamic acid solution formed by the above polymerization reaction. Stirring was continued for an additional 12 hours at room temperature.

The 6FDA-1,3-PDA/3,3'-DDS polyimide solution obtained from the above polymerization reaction, was then slowly poured into a vessel containing 1200 ml methanol. The polyimide 6FDA-1,3-PDA/3,3'-DDS thus precipitated, was then filtered from the solution, and dried in a vacuum oven at 150° C. for 24 hours.

Membranes were prepared from a 6 wt-% solution of 6FDA-1,3-PDA/3,3'-DDS polyimide copolymer in methylenechloride. This solution was cast on a Petri-dish and the solvent was allowed to evaporate at room temperature for 24 hours. The membranes obtained were dried in a vacuum oven, first at 100° C. for 12 hours and then at 150° C. for 12 hours, and, finally at 200° C. for 48 hours before use.

(2) 6FDA-BisAPAF/HAB (1:1)

FORMULA 17

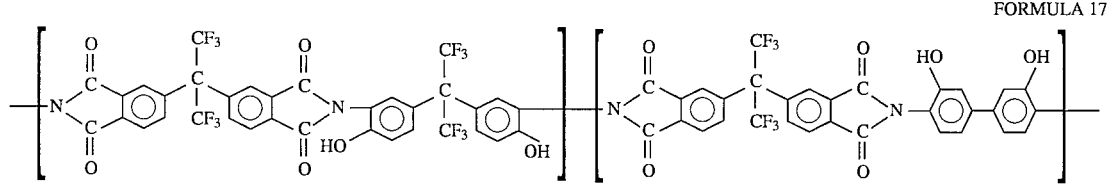

This polyimide copolymer was prepared by polycondensation followed by high-temperature solution imidization. In a reaction vessel, a mixture of 0.01 moles (3.64 g) of BisAPAF and 0.01 moles (2.162 g) of HAB was dissolved in 40 ml NMP over a period of thirty minutes, at room temperature under a constant purge using dry nitrogen. A quantity of 0.02 moles (8.885 g) of 6FDA was added at once to the diamine solution with a vigorous stirring. An additional 30 ml of NMP was then added. The resulting mixture was stirred for 4 hours at room temperature with the reaction mixture vessel was continuously purged using dry nitrogen. This reaction produced a solution of 6FDA-BisAPAF/HAB (1:1) polyamic acid.

FORMULA 16

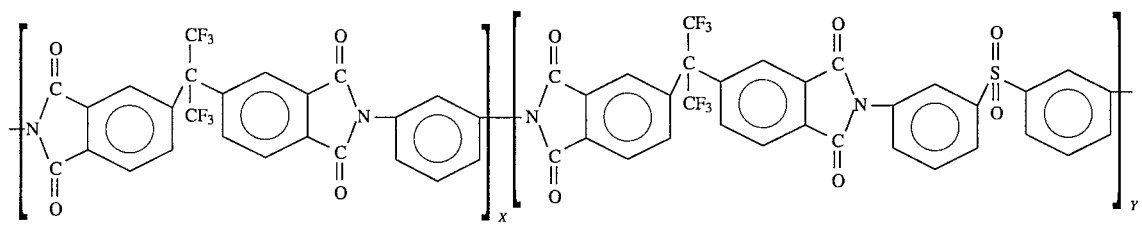

This polyimide copolymer was prepared by polycondensation followed by chemical imidization. A solution containing a mixture of 0.01 moles (1.081 g) of 1,3-PDA and 0.01 moles (2.483 g) of 3,3'-DDS in 30 ml anhydrous NMP was prepared in a reaction vessel at room temperature under a nitrogen atmosphere. An equimolar amount of 6FDA, 0.02 moles (8.883 g), was added as a powder to the above diamine solution while stirring continuously. An additional 25 ml of NMP was then added. The resulting mixture was stirred for about 9 hours at room temperature while the reaction vessel was continuously purged using dry nitrogen. A quantity of 0.10 moles (9.41 ml) acetic anhydride and of The polyamic acid was diluted with 50 ml NMP and stirred for 30 minutes. A quantity of 0.10 moles (10.8 ml) toluene, as a low boiling azeotropic agent, was added to the resulting mixture, and azeotropic distillation was performed at 150°–160° C. Stirring was continued at 170° C. for 12 hours. The solution was gradually cooled to room temperature. The resulting polyimide solution was then slowly poured into a vessel containing 1500 ml methanol. The polyimide copolymer 6FDA-BisAPAF/HAB (1:1) thus precipitated, was then filtered from the solution, dried, redissolved in NMP, and precipitated again with methanol. Finally, the polyimide was filtered from solution and dried first at 150° C. in an air oven for 24 hours and then in a vacuum oven for 48 hours.

Membranes were prepared from a 5–7 wt-% solution of 6FDA-BisAPAF/HAB (1:1) polyimide in methylethylketone. This solution was cast on a Petri-dish and the solvent was allowed to evaporate at room temperature for 24 hours. The membranes were removed by immersing the Petri-dish in hot water and were dried in a vacuum oven consecutively at 100° C., 150° C., and 200° C. for 6 hours each, and finally at 250° C. for 48 hours before use.

(3) 6FDA-2,4-DAPhol/1,3-PDA (3:1)

(1) 6FDA-3,3'-DDS (or 6FDA-m-DDS)

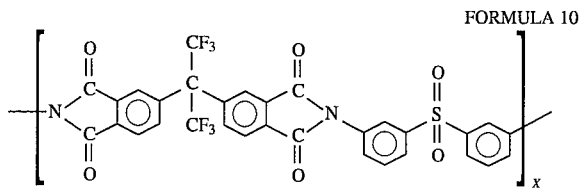

FORMULA 10

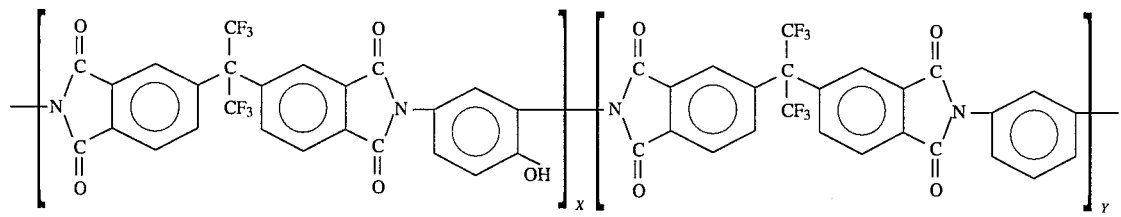

FORMULA 18

This polyimide copolymer was synthesized by polycondensation followed by high-temperature solution imidization. In a reaction vessel, 0.015 moles (2.956 g) of 2,4-DAPhol.2HCl salt was dissolved in 20 ml NMP at room temperature under constant purging with dry nitrogen. To this solution an equimolar amount of $Li_2CO_3$ (1.110 g) in 10 ml NMP was added to neutralize the salt solution; this was stirred for 30 minutes. A quantity of 0.005 moles (0.541 g) 1,3-PDA and of 10 ml of NMP were then added. A quantity of 0.02 moles (8.885 g) of 6FDA was added in one batch to the diamine solution while stirring vigorously. An additional 20 ml of NMP was added to the reaction mixture. The resulting mixture was stirred for 12 hours at room temperature, with the reaction mixture vessel continuously purged using dry nitrogen. This reaction produced a solution of 6FDA-2,4-DAPhol/1,3-PDA polyamic acid.

A quantity of 0.28 moles (30 ml) toluene, as a low boiling azeotropic agent, was added to the above polyamic acid solution and azeotropic distillation was carried out at 150°–160° C. Stirring was continued at 170° C. for 4 hours. The solution was gradually cooled to room temperature. The resulting polyimide solution was then added dropwise to a vessel containing 1200 ml methanol. The polyimide 6FDA-2,4-DAPhol/1,3-PDA (3:1) thus precipitated, was then filtered from the solution, washed with methanol several times, and dried at room temperature in an air oven for 24 hours followed by drying in a vacuum oven at 170° C. for 12 hours.

Membranes were prepared from a 6 wt-% solution of 6FDA-2,4-DAPhol/1,3-PDA polyimide copolymer in acetone. This solution was cast on a Petri-dish and the solvent was allowed to evaporate at room temperature for 24 hours. The membranes obtained were dried in a vacuum oven at 100° C. for 12 hours, then at 150° C. for 12 hours, and finally at 200° C. for 48 hours before use.

IV. Synthesis of Polyimides Used for the Preparation of Polyimide Blends and Membrane Preparation The procedure for the synthesis of 6FDA-3,5-DABAc polyimide used for the preparation of 6FDA-3,5-DABAc/6FDA-1,3,5-TrMPDA polyimide blends of different composition is described above. The polyimide homopolymers 6FDA-3,3'-DDS, 6FDA-1,3-PDA, and 6FDA-1,3,5-TrMPDA used for the preparation of polyimide blends were synthesized as follows:

This polyimide was prepared by polycondensation followed by chemical imidization. A solution of 0.02 moles (4.325 g) of 3,3'-DDS in 30 ml DMAc was prepared in the reaction vessel under a continuous purge using dry nitrogen. A solution containing 0.02 moles (8.883 g) of 6FDA in 35 ml DMAc was then slowly added at 60° C. through a separatory funnel under constant stirring. The resulting mixture was stirred for 3 hours at 60° C., with the reaction vessel continuously purged with dry nitrogen.

A quantity of 0.10 moles (9.41 ml) acetic anhydride and 0.10 moles (13.4 ml) triethyl amine was added to the polyamic acid solution formed by the above polymerization reaction. Stirring was continued for 16 hours at 60° C. The resulting polyimide solution was then slowly poured into a vessel containing 2000–3000 ml methanol. The polyimide 6FDA-3,3'-DDS thus precipitated was then filtered from the solution, dried, redissolved in DMAc, and precipitated again with methanol. Finally, the polyimide was filtered again from solution and dried in a vacuum oven at 100° C. for 48 hours.

(2) 6FDA-1,3-PDA (or 6FDA-m-PDA)

FORMULA 19

This polyimide was prepared by polycondensation followed by chemical imidization. A solution containing 0.02 moles (2.163 g) of 1,3-PDA in 60 ml anhydrous DMAc was prepared in a reaction vessel at room temperature under a nitrogen atmosphere. An equimolar amount of 6FDA (0.02 moles=8.883 g), was added in powder form to the above diamine solution while stirring continuously. The resulting mixture was stirred for about 5 hours at room temperature, with the reaction vessel continuously purged with nitrogen. A quantity of 0.10 moles (9.41 ml) acetic anhydride and 0.10 moles (13.4 ml) triethyl amine was then added to the polyamic acid solution formed by the above polymerization reaction. Stirring was continued for an additional 5 hours at room temperature.

The 6FDA-1,3-PDA polyimide solution obtained from the above polymerization reaction was slowly poured into a vessel containing 1200 ml methanol. The polyimide 6FDA-1,3-PDA thus precipitated was then filtered from the solution and dried in a vacuum oven at 150° C. for 24 hours.

(3) 6FDA-1,3,5-TrMPDA (or 6FDA-1,3,5-TrMPDA)

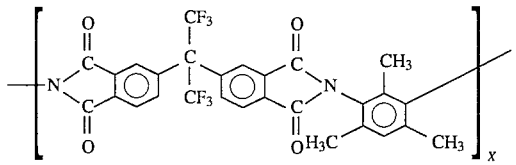

FORMULA 20

This polyimide was prepared by polycondensation followed by chemical imidization. A solution containing 0.02 moles (3.000 g) of 1,3,5-TrMPDA in 30 ml anhydrous DMAc was prepared in a reaction vessel at room temperature in an atmosphere of nitrogen. An equimolar amount of 6FDA (0.02 moles=8.883 g) was added in powder form to the above diamine solution under continuous stirring. An additional 30 ml DMAc was added to the reaction mixture. The resulting mixture was stirred for about 8 hours at room temperature, during which time the reaction vessel was continuously purged with nitrogen. A quantity of 0.10 moles (9.41 ml) acetic anhydride and 0.10 moles (13.4 ml) triethyl amine was added to the polyamic acid solution formed by the above polymerization reaction. Stirring was continued for an additional 5 hours at room temperature.

The 6FDA-1,3,5-TrMPDA polyimide solution, obtained from the above polymerization reaction, was slowly poured into a vessel containing 1200 ml methanol. The polyimide 6FDA-2,4,6-TrMPDA thus precipitated was then filtered from the solution, and dried in a vacuum oven at 150° C. for 24 hours.

(4) 6FDA-3,3'-DDS (or 6FDA-m-DDS)/6FDA-1,3-PDA (or 6-FDA-m-PDA) (50:50) Blend

This blend was prepared by physically mixing 6FDA-3,3'-DDS and 6FDA-1,3-PDA polyimides (1:1 by weight).

Membranes were prepared from a 5-7 wt-% solution of 6FDA-3,3'-DDS/6FDA-1,3-PDA (50:50) polyimide blend in dichloromethane. This solution was cast on a Petri dish and the solvent was allowed to evaporate at room temperature for 24 hours. The membranes were removed by immersing the Petri dish in hot water, and were dried in a vacuum oven at 100° C., 150° C., and 200° C. for 6 hours at each temperature, followed by a final drying at 250° C. for 24 hours before use.

(5) 6FDA-3,5-DABAc/6FDA-1,3,5-TrMPDA (25:75) Blend

This blend was prepared by physically mixing 6FDA-3,5-DABAc and 6FDA-2,4,6-TrMPDA polyimides ( 1:3 by weight).

Membranes were prepared from a 5-7 wt-% solution of 6FDA-3,5-DABAc/6FDA-1,3,5-TrMPDA (25:75) polyimide blend in acetone. The solution was cast on a Petri dish and the solvent was allowed to evaporate at room temperature for 24 hours. The membranes obtained were dried in a vacuum oven at 100° C., and 150° C. for 12 hours at each temperature, followed by a final drying at 250° C. for 24 hours before use.

(6) 6FDA-3,5-DABAc/6FDA-1,3,5-TrMPDA (50:50) Blend

This blend was prepared by physically mixing 6FDA-3,5-DABAc and 6FDA-2,4,6-TrMPDA polyimides (1:1 by weight).

Membranes were prepared from a 5-7 wt-% solution of 6FDA-3,5DABAc/6FDA-1,3,5-TrMPDA (50:50) polyimide blend in acetone. This solution was cast on a Petri dish and the solvent was allowed to evaporate at room temperature for 24 hours. The membranes obtained were dried in a vacuum oven at 100° C., and 150° C. for 12 hours at each temperature, followed by a final drying at 250° C. for 24 hours before use.

(7) 6FDA-3,5-DABAc/6FDA-1,3,5-TrMPDA (75:25) Blend

This blend was prepared by physically mixing 6FDA-3,5-DABAc and 6FDA-2,4,6-TrMPDA polyimides (3:1 by weight).

Membranes were prepared from a 5-7 wt-% solution of 6FDA-3,5DABAc/6FDA-2,4,6-TrMPDA (75:25) polyimide blend in acetone. This solution was cast on a Petri dish and the solvent was allowed to evaporate at room temperature for 24 hours. The membranes obtained were dried in a vacuum oven at 100° C., and 150° C. for 12 hours at each temperature, followed by a final drying at 250° C. for 24 hours before use.

Gas Permeability and Selectivity of the New Polyimides

The permeabilities of the first group of the new polyimides herein disclosed, namely the first three homopolymers and the first two copolymers, to $H_2$, ($CO_2$, $CH_4$, $O_2$, and $N_2$ at 35.0° C. are listed in Table IV, and compared against cellulose acetate as standard. The selectivities of these polyimides to several gas pairs are listed in Table V, and again compared with cellulose acetate. Measurements were performed in accordance with the standards of the American Society for Testing Materials. The polyimides were in the form of dense (symmetric), pinhole-free membranes (films). The apparatus and experimental procedure used in the permeability measurements are well known in the art. The experimental error in the permeability coefficients has been estimated to be ±8–12%, the error being larger the lower the gas permeability.

The permeability coefficients were found to be independent, or to be weak functions, of the pressure difference across the polyimide membranes under the experimental conditions employed. In these measurements the "upstream" pressure was varied from about 20 to over 100 psia (~1.4 to over 6.8 atm), whereas the "downstream" pressure was always near atmospheric pressure. The selectivity values listed in Table VI were obtained at Δp=100 psia (6.8 atm).

TABLE IV

| Gas Permeability Coefficients of New Polyimides at 35° C. | | | | | |
|---|---|---|---|---|---|
| Polymer | $\bar{P}(H_2)$ | $\bar{P}(CO_2)$ | $\bar{P}(CH_4)$ | $\bar{P}(O_2)$ | $\bar{P}(N_2)$ |
| 6FDA-HAB | 24.3 | 5.93 | 0.078 | 1.61 | 0.173 |
| 6FDA-3,3'-DABz[a] | 95.3 | 41.1 | 0.680 | 5.40 | 1.01 |
| 6FDA-3,3'-DABz[b] | n.a. | 22.3 | 0.253 | n.a. | n.a. |
| 6FDA-3,3'-DDS | n.a. | 1.72 | 0.021 | 0.637 | 0.080 |
| 6FDA-4,4'-ODA/DABA(1:1)[c] | 16.0 | 4.56 | 0.0786 | 1.07 | 0.201 |
| 6FDA-4,4'-ODA/DABS(1:1)[c] | 16.1 | 5.84 | 0.123 | 1.45 | 0.246 |
| Cellulose Acetate[d] | 15.5 | 6.56 | 0.20 | 1.46 | 0.230 |

Units: $\bar{P} \times 10^{10}$ [$cm^3$(STP) · cm/s · $cm^2$ · cmHg)
Pressure difference across membrane: 100 psia (6.8 atm);
"Downstream pressure~14.7 psia (1 atm.)
[a] Membrane cured at 200° C. for 5 hrs, next at 300° C. for 2 hrs.
[b] Membrane cured at 200° C. for 5 hrs, next at 300° C. for 24 hrs.
[c] Copolymer ratio 1:1.
[d] A. C. Puleo and D. R. Paul, J. Membrane Sci., 47, 301 (1989), Pressure: 1 atm; Degree of substitution 2.85

Gas permeability and selectivity data for cellulose acetate are included in Tables IV and V, as mentioned, for comparison. Cellulose acetate membranes are being used extensively at present for the separation of $CO_2$ from natural gas. The data for cellulose acetate in Tables IV and V were obtained with dense (symmetric) membranes. It is seen that the new polyimide homopolymers and copolymers have significantly higher gas selectivities for $CO_2$ relative to $CH_4$ than cellulose acetate, as well as comparable or higher permeabilities to $CO_2$. It should be noted that the gas permeability of 6FDA-3,3'-DABz is very sensitive to curing conditions.

TABLE V

Selectivity of New Polyimides Toward Different Gas Pairs at 35° C.

| Polymer | a*($CO_2$/$CH_4$) | a*($O_2$/$N_2$) | a*($H_2$/$CH_4$) | a*($N_2$/$CH_4$) |
|---|---|---|---|---|
| 6FDA-HAB | 76 | 9.3 | 310 | 2.2 |
| 6FDA-3,3'-DABz[a] | 60 | 5.4 | 140 | 1.5 |
| 6FDA-3,3'-DABz[b] | 88 | n.a. | n.a. | n.a. |
| 6FDA-3,3'-DDS | 81 | 7.9 | n.a. | 3.7 |
| 6FDA-4,4'-ODA/DABA(1:1)[c] | 58 | 5.3 | 203 | 2.6 |
| 6FDA-4,4'-ODA/DABS(1:1)[c] | 48 | 5.9 | 132 | 2.0 |
| Cellulose Acetate[d] | 33 | 6.35 | 78 | 1.2 |

Units: a*(A/B) = $\bar{P}$(A)/$\bar{P}$(B).
Pressure difference across membrane: 100 psia (6.8 atm);
"Downstream pressure–14.7 psia (1 atm.)
[a]Membrane cured at 200° C. for 5 hrs, next at 300° C. for 2 hrs.
[b]Membrane cured at 200° C. for 5 hrs, next at 300° C. for 24 hrs.
[c]Copolymer ratio 1:1.
[d]A. C. Puleo and D. R. Paul, J. Membrane Sci., 47, 301 (1989), Pressure: 1 atm; Degree of substitution 2.85

All measurements reported in Tables IV and V were made with pure gases. Since $CO_2$ plasticizes many polymers and may decrease their gas selectivity, it was found necessary to determine the gas permeability and selectivity for $CO_2$ and $CH_4$ of the new polyimides with $CO_2$/$CH_4$ mixtures.

Table VI shows $CO_2$/$CH_4$ selectivity obtained with gas mixtures of approximately 90 mole-% $CO_2$ and 10 mole-% $CH_4$, with measurements being made at 32°–35° C. and 200 psia. The $CO_2$/$CH_4$ selectivity obtained with these gas mixtures is higher than found with pure gases in 6FDA-HAB. The $CO_2$/$CH_4$ selectivity obtained with the 90/10 $CO_2$/$CH_4$ mixture in 6FDA-3,3'-DABz was about the same or somewhat lower than determined with the pure gases, depending on the curing conditions of the polymer, as seen in Table IV. Hence, the polyimides were not significantly plasticized by the $CO_2$ in the 90/10 $CO_2$/$CH_4$ mixture.

TABLE VI

Gas Selectivity of First Group of Polyamides to $CO_2$/$CH_4$ Mixtures[a]

| Polyimide | Sample No. | Permeability Coefficients* $\bar{P}$($CH_4$) | $\bar{P}$($CO_2$) | Selectivity** a*($CO_2$/$CH_4$) |
|---|---|---|---|---|
| 6FDA-3,3'-DABz | B-1 | 21.3 | 0.383 | 55 |
| 6FDA-3,3'-DABz | B-4 | 88.6 | 1.79 | 49 |
| 6FDA-3,3'-DABz | B-5 | 45.9 | 0.845 | 54 |
| 6FDA-HAB | D-1 | 8.43 | 0.0869 | 97 |
| Cellulose Acetate[a] |  | 6.56 | 0.200 | 33 |

Units of Permeability Coefficient: $\bar{P} \times 10^{10}$[cm$^3$(STP) · cm/(s · cm$^2$ · cmHg)]
Feed composition, 90 mole-% $CO_2$/10 mole-% $CH_4$
Temperature: 32–35° C.; Pressure: 200 psia.
[a]A. C. Puleo and D. R. Paul, J. Membrane Sci., 47, 301 (1989).

Table VII shows the permeability and selectivity of the second group of polyimides herein disclosed to several gas pairs. In table VII the GFDA-HAB is the soluble version as produced by the method herein described for the second group. Again, values for cellulose acetate are presented for comparison.

TABLE VII

Permeability and Selectivity of Second Group of Polyimides to Several Gas Pairs

| Polymer | $\bar{P}$($CO_2$) | $\bar{P}$($CO_2$)/$\bar{P}$($CH_4$) | $\bar{P}$($O_2$) | $\bar{P}$($O_2$)/$\bar{P}$($N_2$) | $\bar{P}$($H_2$) | $\bar{P}$($H_2$)/$\bar{P}$($CH_4$) |
|---|---|---|---|---|---|---|
| 6FDA-HAB (Soluble) | 6.3 | 90 | 1.8 | 7.5 | n.a. | n.a. |
| 6FDA-2,4-DAPhol | 8.5 | 94 | 2.4 | 7.1 | 40.2 | 450 |
| 6FDA-3,5-DABAc | 5.2 | 65 | 1.5 | 7.1 | 27.2 | 340 |
| 6FDA-3,3'-DDS/6FDA-1,3-PDA(50/50) | 3.8 | 72 | 1.18 | 7.4 | n.a. | n.a. |
| 6FDA-3,5-DABAc/6FDA-1,3,5-TrMPDA(25/75) | 203.9 | 34 | 53.2 | 4.5 | n.a. | n.a. |
| 6FDA-3,5-DABAc/6FDA-1,3,5-TrMPDA(50/50) | 42.5 | 44 | 9.8 | 5.3 | n.a. | n.a. |
| 6FDA-3,5-DABAc/6FDA-1,3,5-TrMPDA(75/25) | 13.6 | 65 | 4.1 | 6.5 | n.a. | n.a. |
| 6FDA-2,4-DARsol | 8.0 | 74.7 | 2.2 | 7.4 | n.a. | n.a. |
| 6FDA-1,3-PDA/3,3'-DDS(1:1) | 3.3 | 88.3 | 1.0 | 7.9 | 21.3 | 326 |
| 6FDA-BisAPAF/HAB(1:1) | 7.0 | 80.9 | 1.4 | 7.0 | n.a. | n.a. |
| 6FDA-2,4-DAPhol/1,3-PDA(3:1) | 7.2 | 73.0 | 2.1 | 7.3 | 33.6 | 338 |
| Cellulose Acetate[a] | 6.56 | 33 | 1.46 | 6.35 | 15.5 | 78 |

Units: $\bar{P} \times 10^{10}$: [cm$^3$(STP) · cm/(s · cm$^2$ · cmHg)];
Temperature: 95.0° F. (35.0° C.);
$\Delta p$ = 100 psia (6.8 atm).
a*(A/B) = $\bar{P}$(A)/$\bar{P}$(B).
[a]A. C. Puleo and D. R. Paul, J. Membrane Sci., 47, 301 (1989).

In order to be of commercial value, it is necessary that membrane materials exhibit both a sufficiently high $CO_2$/$CH_4$ selectivity and a high $CO_2$ permeability for the separation of $CO_2$/$CH_4$ mixtures to be economically competitive with conventional separation techniques (such as $CO_2$ absorption from natural gas with alkanolamines, or $CO_2$ adsorption on solid adsorbent). The magnitude of the required $CO_2/CH_4$ selectivity and $CO_2$ permeability required must be determined for each application by means of a process design and economic assessment.

Values of the permeability and selectivity of various polyimides to $CO_2/CH_4$ reported in the literature are summarized in Table VIII and FIG. 1.

TABLE VIII

Permeability and Selectivity of Polyamides Towards $CO_2/CH_4$ at 35.0° C.
(Literature Values)

| Sr. No. | Polymer | Test Pressure (atm) | $\bar{P}(CO_2)/\bar{P}(CH_4)$ | $\bar{P}(CO_2) \times 10^{10}$ | Reference |
|---|---|---|---|---|---|
| 1 | PMDA-BATPHF | 10.0 | 26 | 24.6 | 9 |
| 2 | PMDA-BAPHF | 10.0 | 28 | 17.6 | 9 |
| 3 | PMDA-IPDA | 10.0 | 30 | 26.8 | 2 |
| 4 | PMDA-4BDAF | 6.8 | 33 | 11.8 | 5 |
| 5 | PMDA-3BDAF | 6.8 | 36 | 6.1 | 5 |
| 6 | PMDA-4,4'-ODA | 10.0 | 38 | 3.5 | 9 |
| 7 | PMDA-4,4'-ODA | 6.8 | 43 | 1.1 | 5 |
| 8 | PMDA-MDA | 10.0 | 43 | 4.0 | 2 |
| 9 | PMDA-ODA | 10.0 | 46 | 2.7 | 2 |
| 10 | PMDA-3,4'-ODA | 10.0 | 46 | 1.2 | 9 |
| 11 | KAPTON-H(PMDA-based) | 20.0 | 55 | 0.3 | 1 |
| 12 | PMDA-3,3'-ODA | 6.8 | 62 | 0.5 | 5 |
| 13 | BPDA-DATPA | 10.0 | 28 | 4.7 | 8 |
| 14 | BPDA-BATPHF | 10.0 | 33 | 9.2 | 9 |
| 15 | BPDA-BAPHF | 10.0 | 34 | 5.0 | 9 |
| 16 | BPDA-BAHF | 10.0 | 36 | 27.7 | 9 |
| 17 | BPDA-MDA | 10.0 | 41 | 1.6 | 8 |
| 18 | BPDA-DDS | 10.0 | 61 | 2.1 | 8 |
| 19 | BPDA-ODA | 10.0 | 65 | 2.1 | 8 |
|  | Cellulose Acetate | 1.0 | 33 | 6.6 | 6 |
| 20 | BMA-TMPD | 2.0 | 27 | 38.3 | 14 |
| 21 | BTDA-DATPA | 10.0 | 35 | 3.3 | 8 |
| 22 | BTDA-BATPHF | 10.0 | 37 | 6.9 | 9 |
| 23 | BMA-BAPHF | 10.0 | 42 | 4.4 | 9 |
| 24 | BTDA-BAHF | 10.0 | 45 | 10.1 | 9 |
| 25 | BTDA-4,4'-ODA | 10.0 | 57 | 0.6 | 9 |
| 26 | ODPA-DATPA | 10.0 | 34 | 2.9 | 8 |
| 27 | 6FDA-PPDoeP | 6.8 | 7.5 | 15.1 | 11 |
| 28 | 6FDA-PFDoeP | 6.8 | 19 | 8.6 | 11 |
| 29 | 6FDA-PEPE | 6.8 | 27 | 6.9 | 11 |
| 30 | 6FDA-4/3/2BDAF | 6.8 | 30 | 7.5 | 12 |
| 31 | 6FDA-BATPHF | 10.0 | 32 | 22.8 | 9 |
| 32 | PTI4(6FDA-based) | 10.0 | 33 | 8.0 | 13 |
| 33 | PTI3(6FDA-based) | 10.0 | 33 | 8.5 | 13 |
| 34 | 6FDA-DATPA | 10.0 | 34 | 23.0 | 8 |
| 35 | PTII(6FDA-based) | 10.0 | 34 | 17.3 | 13 |
| 36 | PTI2(6FDA-based) | 10.0 | 34 | 9.8 | 13 |
| 37 | 6FDA-4/2BDAF | 6.8 | 34 | 8.9 | 12 |
| 38 | 6FDA-PBEPE | 6.8 | 34 | 2.5 | 11 |
| 39 | 6FDA-BAPHF | 10.0 | 37 | 19.1 | 9 |
| 40 | 6FDA-4BDAF | 6.8 | 37 | 19.0 | 5 |
|  | Cellulose acetate | 1.0 | 33 | 6.6 | 6 |
| 41 | 6FDA-BAHF | 10.0 | 38 | 51.2 | 9 |
| 42 | 6FDA-4BDAF | 6.8 | 38 | 18.9 | 12 |
| 43 | 6FDA-4/3BDAF | 6.8 | 39 | 10.2 | 12 |
| 44 | 6FDA-3BDAF | 6.8 | 40 | 5.7 | 12 |
| 45 | 6FDA-2,4-DATr | 6.8 | 41 | 28.6 | 7 |
| 46 | 6FDA-4,4'-ODA | 6.8 | 41 | 22.0 | 5 |
| 47 | 6FDA-IPDA | 10.0 | 43 | 30.0 | 2 |
| 48 | 6FDA-PTEPE | 6.8 | 43 | 1.9 | 11 |
| 49 | PSI3(6FDA-based) | 10.0 | 44 | 14.4 | 13 |
| 50 | 6FDA-PMDoeP | 6.8 | 45 | 4.8 | 11 |
| 51 | 6FDA-2,6-DATr | 6.8 | 46 | 42.5 | 7 |
| 52 | 6FDA-3,5-DBTF | 6.8 | 48 | 21.6 | 7 |
| 53 | 6FDA-3BDAF | 6.8 | 48 | 6.3 | 5 |
| 54 | 6FDA-4,4'-ODA | 10.0 | 49 | 16.7 | 9 |
| 55 | 6FDA-APAP | 10.0 | 49 | 10.7 | 9 |
| 56 | 6FDA-3,4'-PDA | 10.0 | 49 | 6.1 | 9 |
| 57 | 6FDA-PMeaP | 6.8 | 53 | 2.4 | 11 |
| 58 | 6FDA-DAF | 10.0 | 55 | 21.3 | 3 |
| 59 | 6FDA-MDA | 10.0 | 56 | 24.2 | 2 |
| 60 | 6FDA-ODA | 10.0 | 61 | 23.0 | 2 |
| 61 | 6FDA-3,3'-ODA | 6.8 | 64 | 2.1 | 5 |
|  | Cellulose acetate | 1.0 | 33 | 6.6 | 6 |

Unit: Permeability coefficient, $\bar{P}$ [$cm^3$(STP) · cm/s · $cm^2$ · cm Hg]

A listing of the references used to derive Table VIII follows:

1. K. C. O'Brien, W. J. Koros, and G. R. Husk, Influence of casting and curing conditions on gas sorption and transport in polyimide films, Polym. Eng. Sci., 27 (1987) 211–217.
2. T. H. Kim, W. J. Koros, G. R. Husk, and K. C. O'Brien, Relationship between gas separation properties and chemical structure in a series of aromatic polyimides, J. Membrane Sci., 37 (1988) 45–62.
3. T. H. Kim, W. J. Koros, G. R. Husk, Temperature effects on gas permselection properties in hexafluoro aromatic polyimides, J. Membrane Sci., 46 (1989) 43–56.
4. K. Tanaka, H. Kita, K. Okamato, A. Nakamura, and Y. Kusuki, Gas permeability and permselectivity in polyimides based on 3,3',4,4'-biphenyltetracarboxylic dianhydride, J. Membrane Sci., 47 (1989) 203–215.
5. S. A. Stern, Y. Mi, and H. Yamamoto, Structure/permeability relationships of polyimide membranes. Applications to the separation of gas mixtures, J. Polym. Sci., Polym. Phys. Ed., 27 (1989) 1887–1909.
6. A. C. Puleo, D. R. Paul, and S. S. Kelley, The effect of degree of acetylation on gas sorption and transport behavior in cellulose acetate, J. Membrane Sci., 47 (1989) 301–332.
7. H. Yamamoto, Y. Mi, S. A. Stern and A. K. St. Clair, Structure/permeability relationships of polyimide membranes. II., J. Polym. Sci., Polym. Phys. Ed., 28 (1990) 2291–2304.
8. K. Okamoto, K. Tanaka, H. Kita, M. Ishida, M. Kakimoto, and Y. Imai, Gas permeability and permselectivity of polyimides prepared from 4,4'-diaminotriphynylamine, Polymer J., 24 (1992) 451–457.
9. K. Tanaka, H. Kita, M. Okano, and K. Okamoto, Permeability and permselectivity of gases in fluorinated and non-fluorinated polyimides, Polymer .33 (1992) 585–592.
10. K. Matsumoto, P. Xu, and T. Nishikimi, Gas permeation of aromatic polyimides. I. Relationship between gas permeabilities and dielectric constants, J. Membrane Sci 81 (1993) 15–22.
11. S. A. Stern, Y. Liu, and W. A. Feld, Structure/permeability relationships of polyimides with branched or extended diamine moieties, J. Polym. Sci., Polym. Phys. Ed., 31 (1993) 939–951.
12. G. Zola, S. A. Stern, A. K. St. Clair and J. R. Pratt, Permeability relationships of polyimide copolymers, J. Polym. Sci., Polym. Phys. Ed., 32 (1994) 53–58.
13. F. P. Glatz, R. Mulhaupt, J. C. Schultze, and J. Springer, Gas permeabilities and permselectivities of amorphous segmented 6F poly (arylene thioether imide)s and the corresponding poly (arylene sulfone imide)s, J. Membrane Sci., 90 (1994) 151–159.
14. H. Kita, T. Inada, K. Tanaka, and K. Okamoto, Effect of photocrosslinking on permeability and permselectivity of gases through benzophenone-containing polyimide, J. Membrane Sci., 87 (1994) 139–147.

Many polyimides (if not most) do not exhibit a sufficiently higher $CO_2/CH_4$ selectivity and $CO_2$ permeability to be competitive with cellulose acetate. This can be clearly seen in Table VIII and FIG. 1. Cellulose acetate membranes are currently used on a large scale for the removal of $CO_2$ from natural gas and from other mixtures containing $CH_4$. Many polyimides, however, actually possess lower $CO_2/CH_4$ selectivity and/or $CO_2$ permeability than does cellulose acetate.

The polyimides of the instant invention demonstrate 2 to 3 times higher selectivity for $CO_2/CH_4$, and an equal or higher $CO_2$ permeability compared to cellulose acetate as seen in Tables IV and VII and FIG. 1. Most of the polyimides of the invention exhibit both a significantly higher $CO_2/CH_4$ selectivity and $CO_2$ permeability compared to the values reported for most other polyimides and for cellulose acetate, as seen in FIG. 1.

The data in Tables IV through VII and FIG. 1 were determined using pure $CO_2$ and $CH_4$. However, the gas selectivity and permeability of many polymers determined with gas mixtures containing components (such as $CO_2$) that plasticize ("swell") the membranes, can be significantly different from those determined with pure gases. Therefore, the $CO_2/CH_4$ selectivity, and in some cases the $H_2S/CH_4$ selectivity as well as the permeability to $CO_2$ and $H_2S$ of some of the polyimides of the instant invention were determined using different $CH_4/CO_2$ and $CH_4/CO_2/H_2S$ gas mixtures. The results are shown in Tables IX through XII. Mixtures with $H_2S$ were studied because this gas is found in some low-quality natural gas streams.

TABLE IX

Comparison of Permeability and Selectivity of Some Polyamides Towards $CO_2/CH_4$ Determined With Pure Gases and Gas Mixture

| Polyimide | Selectivity, $CO_2/CH_4$ | | Permeability, $\bar{P}(CO_2) \times 10^{10}$ | |
| --- | --- | --- | --- | --- |
| | Pure gas[a] | Gas mixture[b] | Pure gas[a] | Gas mixture[b] |
| 6FDA-3,5-DAPhol | 94 | 79 | 8.5 | 6.8 |
| 6FDA-HAB (Soluble) | 90 | 85 | 6.3 | 7.2 |
| 6FDA-DABz | 88 | 45 | 22.3 | 29.2 |
| 6FDA-3,3'-DDS | 81 | 78 | 1.7 | 2.5 |

Unit: Permeability coefficient, $\bar{P}$ [cm³(STP) · cm/s · cm² · cmHg]
[a]Measurements made at 95.0° F. (35.0° C.) and at a pressure of 100.0 psia (6.8 atm) with pure gases.
[b]Measurements made at 95.0° F. (35.0° C.) and at a feed pressure of 147.0 psia (10.0 atm) with a binary gas mixture containing 90 mole-% $CH_4$ and 10 mole-% $CO_2$

TABLE X

Permeability and Selectivity of 6FDA-HAB Polyimide Towards $CH_4/CO_2/H_2S$ and $CH_4/CO_2$ Mixtures[a]

| Composition | Selectivity | | Permeability, $\bar{P} \times 10^{10}$ | | |
| --- | --- | --- | --- | --- | --- |
| (Mole-%) | $CO_2/CH_4$ | $H_2/CH_4$ | $CO_2$ | $CH_4$ | $H_2S$ |
| (87.5/9.7/2.8) | 94 | 16 | 6.4 | 0.068 | 1.1 |
| (90/10) | 85 | — | 7.3 | 0.086 | — |
| (65.3/27.4/7.3) | 84 | 15 | 3.8 | 0.045 | 0.69 |
| (70/30) | 64 | — | 5.7 | 0.089 | — |
| (55.3/36.7/8) | 80 | 15 | 4.2 | 0.053 | 0.78 |
| (60/40) | 59 | — | 6.1 | 0.103 | — |

Unit: Permeability coefficient, $\bar{P}$ [cm³(STP) · cm/s · cm² · cmHg]
[a]Measurements made at 95.0° F. (35.0° C.) and at a feed pressure of 147.0 psia (10 atm)

TABLE XI

Permeability and Selectivity of 6FDA-4,4'-PDA Polyimide for $CH_4/CO_2/H_2S$ and $CH_4/CO_2$ Mixtures[a]

| Composition | Selectivity | | Permeability, $\bar{P} \times 10^{10}$ | | |
|---|---|---|---|---|---|
| (Mole-%) | $CO_2/CH_4$ | $H_2/CH_4$ | $CO_2$ | $CH_4$ | $H_2S$ |
| (87.5/9.7/2.8) | 60 | 11 | 21.9 | 0.366 | 4.0 |
| (90/10) | 58 | — | 22.4 | 0.385 | — |

Unit: Permeability coefficient, $\bar{P}$ [$cm^3$(STP) · cm/s · $cm^2$ · cmHg]
[a]Measurements made at 95.0° F. (35.0° C.) and at a feed pressure of 147.0 psia (10 atm)

TABLE XII

Permeability and Selectivity of 6FDA-1,3-PDA Polyimide for $CH_4/CO_2/H_2S$ and $CH_4/CO_2$ Mixtures[a]

| Composition | Selectivity | | Permeability, $\bar{P} \times 10^{10}$ | | |
|---|---|---|---|---|---|
| (Mole-%) | $CO_2/CH_4$ | $H_2/CH_4$ | $CO_2$ | $CH_4$ | $H_2S$ |
| (87.5/9.7/2.8) | 60 | 7 | 8.8 | 0.145 | 1.1 |
| (90/10) | 61 | — | 9.3 | 0.152 | — |

Unit: Permeability coefficient, $\bar{P}$ [$cm^3$(STP) · cm/s · $cm^2$ · cmHg]
[a]Measurements made at 95.0° F. (35.0° C.) and at a feed pressure of 147.0 psia (10 atm)

Table IX shows that the values of $CO_2/CH_4$ selectivity and $CO_2$ permeability of the polyimides studied using pure gases are different from the values obtained with gas mixtures. Moreover, in some cases the presence of $H_2S$ increases the $CO_2/CH_4$ selectivity significantly, as shown in the results of Tables X–XII. This effect is unexpected and not predictable.

The general order of permeability of the polyimides of the instant invention to gases tested is: $He > H_2 > CO_2 > O_2 > N_2 > CH_4$.

Economic assessments of membrane separation processes for the removal of $CO_2$ and $H_2S$ from natural gas were made for three of the polyimide membranes disclosed herein. For comparison, similar calculations were also made assuming that cellulose acetate was the membrane material utilized for this process. The economic assessments assumed a set of "base-case" conditions, shown in Table XIII, that are representative of an average acid gas ($CO_2$ and $H_2S$) removal plant. The details of the procedures used in estimating the processing costs are reported in the literature [Ref. B. D. Bhide and S. A. Stern, *J. Membrane Sci.*, 81 (1993) 209–237; ibid, 239–252.].

TABLE XIII

Base-case Operating Conditions

| | |
|---|---|
| Feed gas flow rate: | 35 MMSCFD (million standard $ft^3$/day) |
| Feed composition: | 10–40 mole-% $CO_2$, balance $CH_4$ |
| Retentate composition: | $\leq 2$ mole-% $CO_2$, balance $CH_4$ |
| Effective membrane thickness: | 0.004 mil (1000 Å) |
| Feed pressure: | 800 psia |
| Permeate pressure: | 20 psia |

Table XIV shows that the natural gas processing costs for the polyimide membranes are significantly lower than those for cellulose acetate membranes. Membrane processes for the removal of $CO_2$ from natural gas based on other polyimides with lower $CO_2/CH_4$ selectivities and $CO_2$ permeabilities than the polyimides of the instant invention are not competitive or only marginally competitive with processes based on cellulose acetate membranes.

TABLE XIV

Economic Assessments for the Membrane Process for the Removal of $CO_2$ from Natural Gas
Comparison of New Polyamides and Cellulose acetate Membranes

| | Processing Costs, ($/MSCF) | | |
|---|---|---|---|
| $CO_2$ in Feed (Mole-%) | 6FDA-HAB | 6FDA-DABz | Cellulose acetate |
| 10 | 0.195 | 0.106 | 0.221 |
| 20 | 0.267 | 0.147 | 0.299 |
| 30 | 0.287 | 0.158 | 0.313 |
| 40 | 0.284 | 0.168 | 0.304 |

While this invention has been explained with reference to the structure disclosed herein, it is not confined to the details set forth and this application is intended to cover any modifications and changes as may come within the scope of the following claims:

We claim:

1. A process for separating a first gas, which is $CO_2$, from a second gas, which is $CH_4$, comprising the steps of:

(1) contacting one side of a semi-permeable gas separation membrane with a feed gas mixture containing at least the first gas and the second gas, wherein the membrane divides a separation chamber into a high-pressure side, into which the feed gas mixture is fed, and a low-pressure side;

(2) maintaining a pressure differential across the membrane under conditions such that the first gas in the feed gas mixture selectively permeates through the membrane from the high-pressure side to the low-pressure side of the membrane;

(3) removing from the low-pressure side of the membrane permeated gas mixture which is enriched in the first gas and depleted in the second gas; and (4) removing from the high-pressure side of the membrane a gas mixture which is enriched in the second gas and depleted in the first gas;

wherein the membrane comprises at least in part a thin discriminating layer of polyimide having the repeating formula

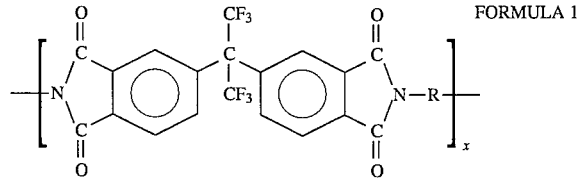

FORMULA 1 wherein R is:

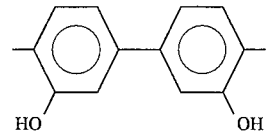

FORMULA 2

OR

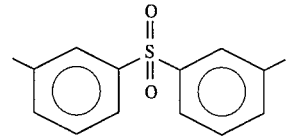

FORMULA 3

FORMULA 4

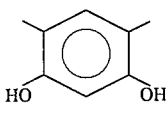

OR

FORMULA 5

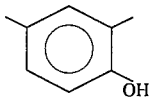

OR

FORMULA 6

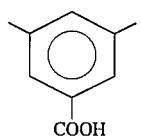

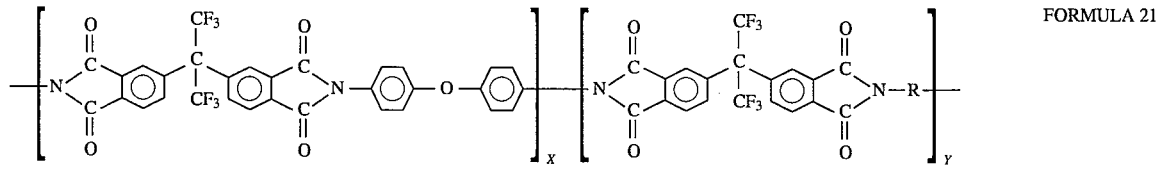
FORMULA 21 and x is an integer.

2. A process for separating a first gas, which is $CO_2$, from a second, gas which is $CH_4$, comprising:

(1) contacting one side of a semi-permeable gas separation membrane with a feed gas mixture containing at least the first gas and the second gas, wherein the membrane divides a separation chamber into a high-pressure side into which the feed gas mixture is fed and a low-pressure side;

(2) maintaining a pressure differential across the membrane under conditions such that the first gas in the feed gas mixture selectively permeates through the membrane from the high-pressure side to the low-pressure side of the membrane;

(3) removing from the low-pressure side of the membrane permeated gas mixture which is enriched in a first gas and depleted in the second gas; and (4) removing from the high-pressure side of the membrane a gas mixture which is enriched in the second gas and depleted in the first gas;

wherein the membrane comprises at least in part a thin discriminating layer of polyimide having the repeating formula:

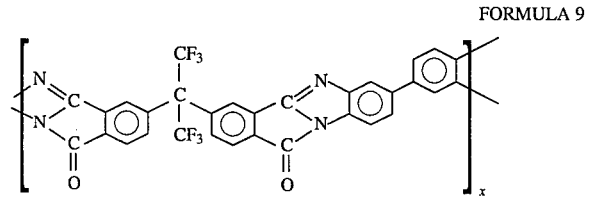
FORMULA 9

FIG. 7 where x is an integer.

3. A process for separating a first gas, which is $CO_2$, from a second gas which is $CH_4$, comprising:

(1) contacting one side of a semi-permeable gas separation membrane with a feed gas mixture containing at least the first gas and the second gas, wherein the membrane divides a separation chamber into a high-pressure side into which the feed gas mixture is fed and a low-pressure side;

(2) maintaining a pressure differential across the membrane under conditions such that the first gas in the feed gas mixture selectively permeates through the membrane from the high-pressure side to the low-pressure side of the membrane;

(3) removing from the low-pressure side of the membrane permeated gas mixture which is enriched in a first gas and depleted in the second gas; and (4) removing from the high-pressure side of the membrane a gas mixture which is enriched in the second gas and depleted in the first gas;

wherein the membrane comprises at least in part a thin discriminating layer of polyimide having the repeating formula:

where x and y are both integers, and R is

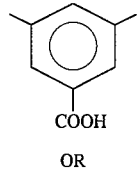
FORMULA 6

OR

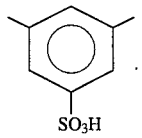
FORMULA 22

4. The process according to claim 3 where

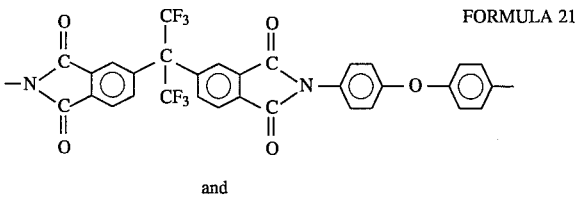
FORMULA 21 and

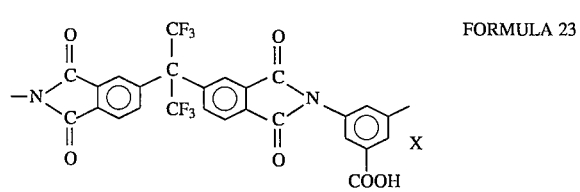
FORMULA 23 are in an overall proportion of 1 to 1.

5. The process according to claim 3 where

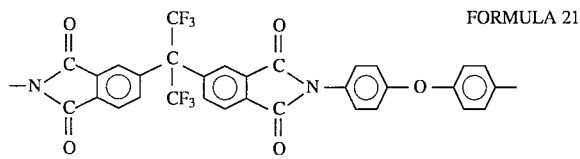 FORMULA 21 and

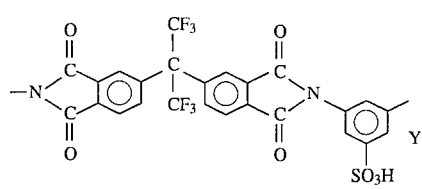 FORMULA 24 are in an overall proportion of 1 to 1.

6. A process for separating a first gas, which is $CO_2$, from a second gas, which is $CH_4$, comprising:

(1) contacting one side of a semi-permeable gas separation membrane with a feed gas mixture containing at least the first gas and the second gas, wherein the membrane divides a separation chamber into a high-pressure side into which the feed gas mixture is fed and a low-pressure side;

(2) maintaining a pressure differential across the membrane under conditions such that the first gas in the feed gas mixture selectively permeates through the membrane from the high-pressure side to the low-pressure side of the membrane;

(3) removing from the low-pressure side of the membrane permeated gas mixture which is enriched in a first gas and depleted in the second gas; and (4) removing from the high-pressure side of the membrane a gas mixture which is enriched in the second gas and depleted in the first gas;

wherein the membrane comprises at least in part a thin discriminating layer of polyimide having the repeating formula:

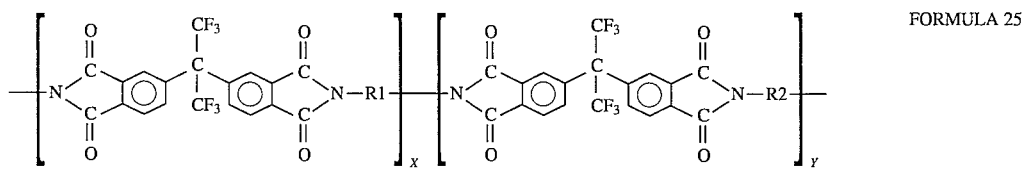 FORMULA 25 where x and y are both integers, and R1 is:

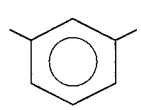 FORMULA 26

OR

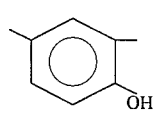 FORMULA 5

OR

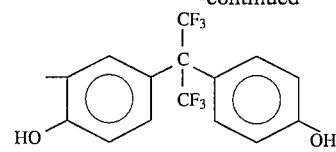 FORMULA 27 and if R1 is, 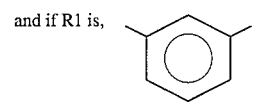 FORMULA 26 then R2 is: 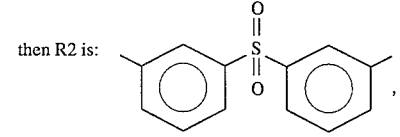 FORMULA 3 , if R1 is, 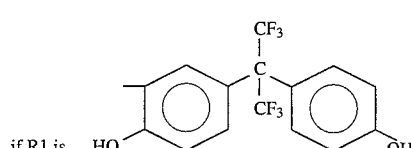 FORMULA 27 then R2 is: 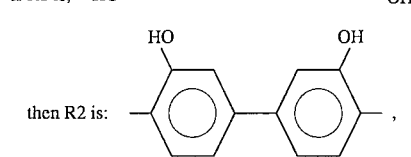 FORMULA 2 , and if R1 is, 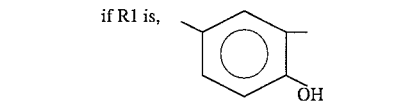 FORMULA 5 then R2 is: 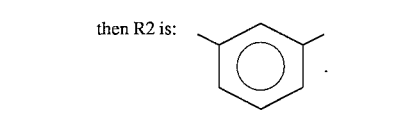 FORMULA 26 .

7. The process according to claim 6 where R1 is:

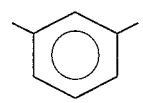 FORMULA 26 and R2 is:

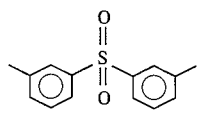 FORMULA 3 and

-continued

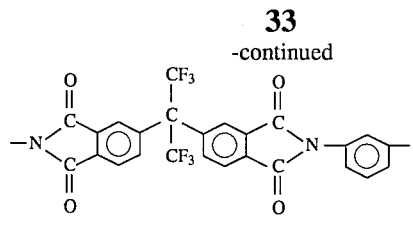

FORMULA 19 and

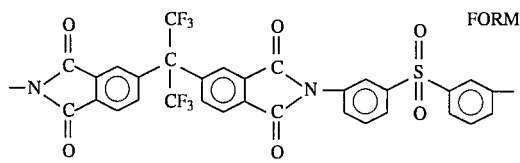

FORMULA 10 are in an overall proportion of 1 to 1.

8. The process according to claim 6 wherein R1 is:

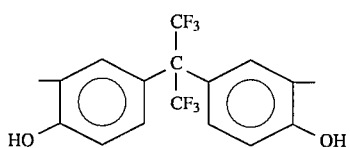

FORMULA 27 and R2 is:

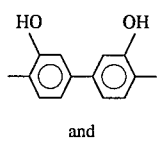

FORMULA 2 and

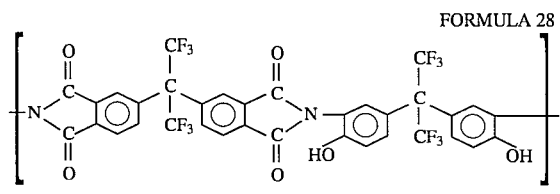

FORMULA 28 and

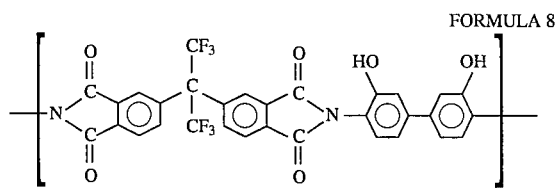

FORMULA 8 are in an overall proportion of 1 to 1.

9. The process according to claim 8 where R1 is:

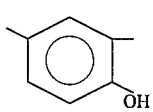

FORMULA 5 and R2 is:

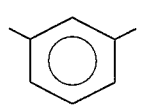

FORMULA 26 and the proportion of

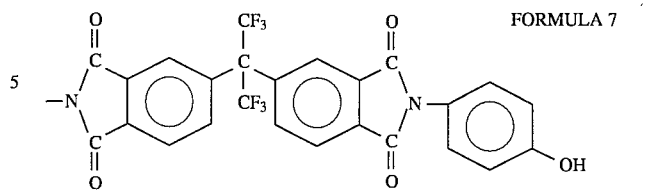

FORMULA 7 to

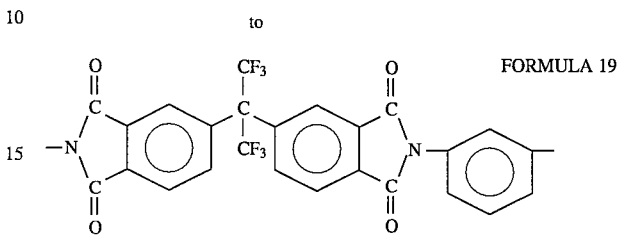

FORMULA 19 is 3 to 1 overall.

10. A process for separating a first gas, which is $CO_2$, from a second gas, which is $CH_4$, comprising:

(1) contacting one side of a semi-permeable gas separation membrane with a feed gas mixture containing at least the first gas and the second gas, wherein the membrane divides a separation chamber into a high-pressure side into which the feed gas mixture is fed and a low-pressure side;

(2) maintaining a pressure differential across the membrane under conditions such that the first gas in the feed gas mixture selectively permeates through the membrane from the high-pressure side to the low-pressure side of the membrane;

(3) removing from the low-pressure side of the membrane permeated gas mixture which is enriched in a first gas and depleted in the second gas; and (4) removing from the high-pressure side of the membrane a gas mixture which is enriched in the second gas and depleted in the first gas;

wherein the membrane comprises at least in part a thin discriminating layer of two blended polyimides, comprising a first polyimide having the repeating formula:

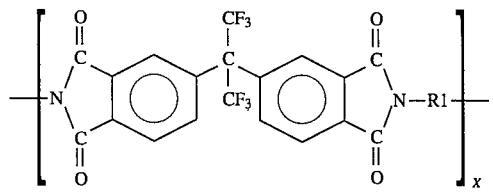

FORMULA 29 and a second polyimide having the repeating formula:

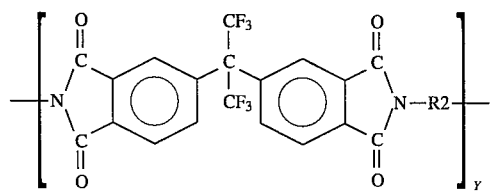

FORMULA 30 where R1 is
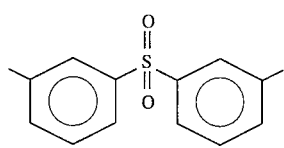
or
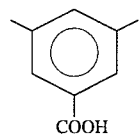
and if R1 is 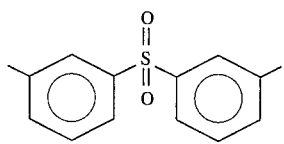
then R2 is 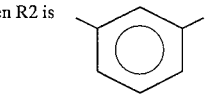
and if R1 is 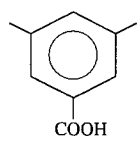
then R2 is 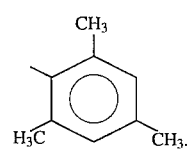
11. The process according to claim 10 where R1 is
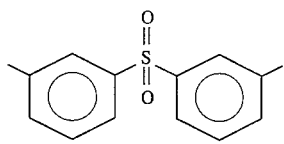 FORMULA 3
and R2 is FORMULA 26
and the ratio of
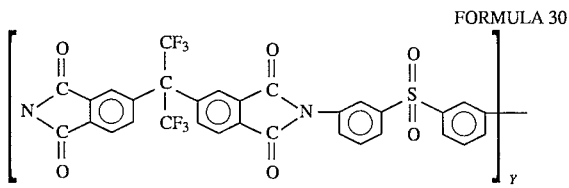 FORMULA 30
to
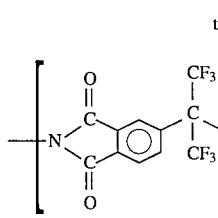 FORMULA 29
is 50:50.
12. The process according to claim 10 where R1 is
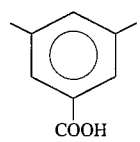 FORMULA 6
and R2 is
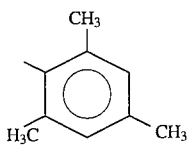 FORMULA 27
and the ratio of
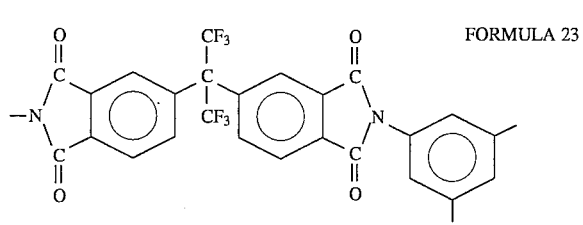 FORMULA 23
to
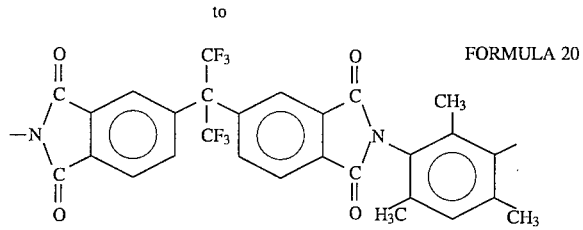 FORMULA 20
is 25:75.
13. The process according to claim 10 where R1 is
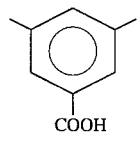 FORMULA 6
and R2 is
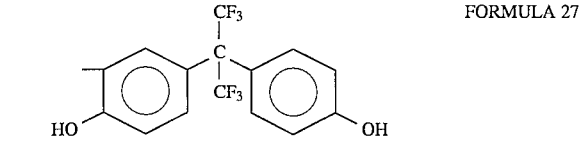 FORMULA 27
and the ratio of
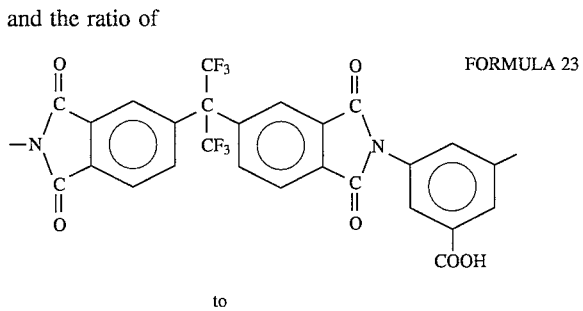 FORMULA 23
to -continued
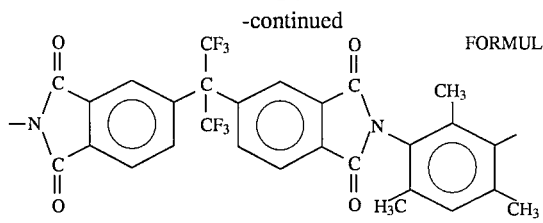
FORMULA 20
is 50:50.
14. The process according to claim 10 where R1 is
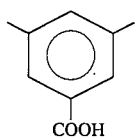
FORMULA 6
and R2 is
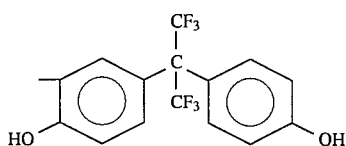
and the ratio of
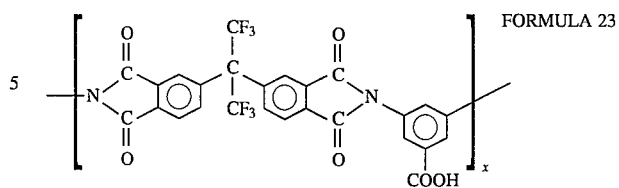
FORMULA 23
to
FORMULA 20
[structure with ratio 75:25]
FORMULA 27
is 75:25.
* * * * *